(12) United States Patent
Suzuki et al.

(10) Patent No.: US 12,708,296 B2
(45) Date of Patent: Aug. 18, 2026

(54) PROBE UNIT

(71) Applicant: HAMAMATSU PHOTONICS K.K., Hamamatsu (JP)

(72) Inventors: Norihiro Suzuki, Hamamatsu (JP); Yukio Ueda, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 317 days.

(21) Appl. No.: 18/564,771

(22) PCT Filed: Mar. 17, 2022

(86) PCT No.: PCT/JP2022/012330
§ 371 (c)(1), (2) Date: Nov. 28, 2023

(87) PCT Pub. No.: WO2022/254883
PCT Pub. Date: Dec. 8, 2022

(65) Prior Publication Data

US 2024/0374182 A1 Nov. 14, 2024

(30) Foreign Application Priority Data

Jun. 2, 2021 (JP) ................................ 2021-092778

(51) Int. Cl.
*A61B 5/00* (2006.01)
*A61B 5/1455* (2006.01)

(52) U.S. Cl.
CPC ...... *A61B 5/14553* (2013.01); *A61B 5/14552* (2013.01); *A61B 2503/045* (2013.01)

(58) Field of Classification Search
CPC ........... A61B 5/14553; A61B 5/14552; A61B 2503/045; A61B 5/0075; A61B 5/6803; A61B 5/6814; A61B 2562/185
See application file for complete search history.

(56) References Cited

U.S. PATENT DOCUMENTS 9,737,213 B1 * 8/2017 Heaton .................... A61B 1/31
12,150,741 B2 * 11/2024 Gopalakrishnan ... A61B 5/6803
(Continued)

FOREIGN PATENT DOCUMENTS

EP 3804618 A1 4/2021
JP S63-275328 A 11/1988
(Continued)

OTHER PUBLICATIONS

International Preliminary Report on Patentability issued Dec. 14, 2023 in PCT/JP2022/012330.
(Continued)

*Primary Examiner* — May A Abouelela
(74) *Attorney, Agent, or Firm* — Faegre Drinker Biddle & Reath LLP

(57) ABSTRACT

A probe unit is a probe unit used to measure hemoglobin dynamics inside a subject, and the probe unit includes a main body having flexibility, a first probe attached to the main body and having a first face from which a first light emitting portion for irradiating the subject with light is exposed, a second probe attached to the main body to face the first probe and having a second face from which a first light incidence portion for detecting light propagated inside the subject is exposed, a first light shielding member having light shielding properties, containing an elastic material, and attached to the first face to surround an emission axis of the first light emitting portion, and a second light shielding member having light shielding properties, containing an elastic material, and attached to the second face to surround an incidence axis of the first light incidence portion.

7 Claims, 15 Drawing Sheets

(56) References Cited

U.S. PATENT DOCUMENTS

| | | | | |
|---|---|---|---|---|
| 2009/0088649 | A1* | 4/2009 | Ninomiya | A61B 5/0059 600/476 |
| 2009/0299160 | A1* | 12/2009 | Moridaira | A61B 5/6814 600/322 |
| 2010/0249557 | A1* | 9/2010 | Besko | A61B 5/6814 600/340 |
| 2010/0292588 | A1 | 11/2010 | Uenishi et al. | |
| 2012/0083673 | A1* | 4/2012 | Al-Ali | A61B 5/374 600/301 |
| 2015/0018651 | A1* | 1/2015 | Benni | A61B 5/746 600/323 |
| 2016/0167672 | A1* | 6/2016 | Krueger | G16H 40/63 340/576 |
| 2016/0278643 | A1* | 9/2016 | Kiguchi | A61B 5/4064 |
| 2016/0310054 | A1* | 10/2016 | Izzetoglu | A61B 5/01 |
| 2017/0311887 | A1 | 11/2017 | Leussler et al. | |
| 2018/0192931 | A1* | 7/2018 | Linden | A61B 5/14552 |
| 2018/0220968 | A1* | 8/2018 | Funane | A61B 5/6803 |
| 2018/0348863 | A1 | 12/2018 | Aimone et al. | |
| 2019/0142316 | A1* | 5/2019 | Esenaliev | A61B 5/6803 600/340 |
| 2019/0261859 | A1* | 8/2019 | Dietiker | A61B 5/0064 |
| 2020/0029875 | A1 | 1/2020 | Hirano et al. | |
| 2020/0163593 | A1* | 5/2020 | Trau | A61B 5/1032 |
| 2020/0281510 | A1* | 9/2020 | Froehlich | A61B 5/6833 |
| 2020/0305731 | A1* | 10/2020 | Yoshitani | A61B 5/0275 |
| 2020/0305778 | A1* | 10/2020 | Vinciguerra | A61B 5/291 |
| 2021/0007607 | A1* | 1/2021 | Frank | A61B 5/14552 |
| 2021/0022613 | A1* | 1/2021 | Connor | A41C 3/0064 |
| 2021/0259583 | A1* | 8/2021 | Sorgenfrei | A61B 5/4064 |
| 2021/0282644 | A1* | 9/2021 | Shah | A61B 5/0073 |
| 2021/0401335 | A1* | 12/2021 | Kamada | A61B 5/14552 |
| 2022/0031169 | A1* | 2/2022 | Vermeulen | A61B 5/0088 |
| 2022/0068505 | A1* | 3/2022 | Junnarkar | H04M 1/2155 |

FOREIGN PATENT DOCUMENTS

| | | | |
|---|---|---|---|
| JP | 2008-200226 | A | 9/2008 |
| JP | 2015-033561 | A | 2/2015 |
| JP | 2016-067482 | A | 5/2016 |
| JP | 2017-023455 | A | 2/2017 |
| JP | 2020-062354 | A | 4/2020 |
| WO | 2009/001449 | A1 | 12/2008 |
| WO | WO-2011/022649 | A1 | 2/2011 |
| WO | WO-2013/161070 | A1 | 10/2013 |

OTHER PUBLICATIONS

Extended European Search Report issued on Apr. 22, 2025 in corresponding European patent application 22815640.2.

* cited by examiner 1B
4
5
52
52a
52b
55
G
31(3)
III
F
7
9
53
10
21(2)
8
6
54
51b
51
51a (a)
Va
21(2)
6
8
61s
22s
21s(2p)
22(2)
8a
8b
A1
61
Va
(b)
Vb
31(3)
7
9
71s
32s
31s(3p)
32(3)
9a
9b
A2
71
Vb

Fig.6
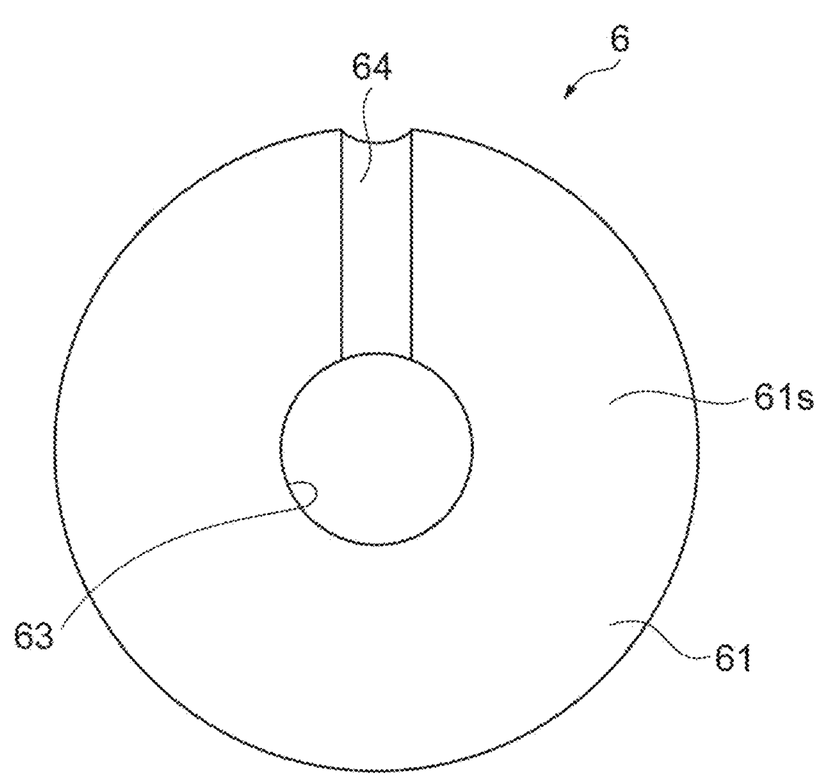
(a)
64
6
61s
63
61
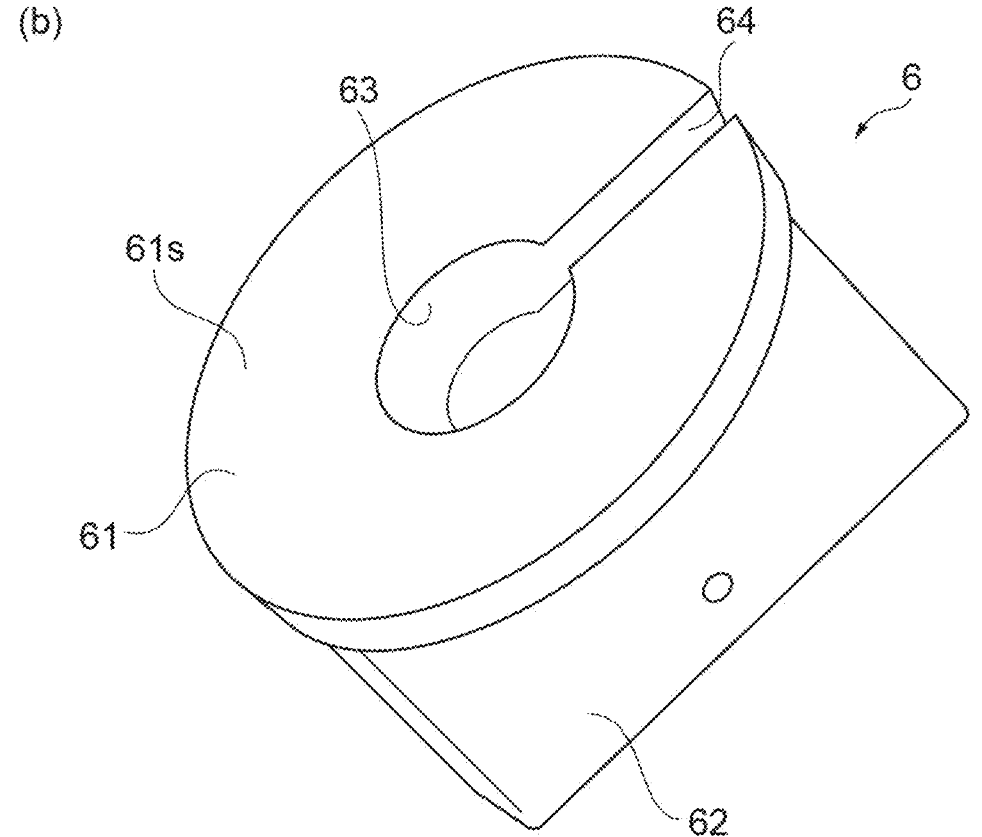
(b)
64
63
6
61s
61
62

1B
Hs
H
Ds
8
8a
8b
6
F
5
5a
A1
62
2p
2
S
61s
5b
F
4
8a
8
8b (a)
(b)
1D
4
2p
2
S1
S2
3
3p
8p
62
61s
6
61
8
9
7
71
71s
72
9p
L1
L2
H
Hs 4
5
5a
5b
6
61
61s
62
F
A1
A2
2
2p
3
3p
S1
S2
8
8a
8b
8p
Ds
Hs
H

PROBE UNIT

TECHNICAL FIELD

The present disclosure relates to a probe unit.

BACKGROUND ART

Patent Literature 1 describes a near-infrared sensor that can be used to measure tissue oxygen saturation in blood or tissue of a patient. The sensor includes a sensor pad having a circuit board on which a light source that generates near-infrared light and a photodetector that detects near-infrared light generated from the light source to pass through a portion of a body of the patient are arranged. The sensor pad further includes a bottom layer provided on the circuit board. The bottom layer is provided with an adhesive for sticking the sensor pad on the patient.

CITATION LIST

Patent Literature

Patent Literature 1: International Publication WO 2011/022649

SUMMARY OF INVENTION

Technical Problem

When measuring the tissue oxygen saturation using the sensor described in Patent Literature 1, it is conceivable to directly stick the sensor pad on the patient using the adhesive provided on the bottom layer. However, when the patient subjected to measurement of the tissue oxygen saturation is, for example, a preterm infant, skin may be immature or underdeveloped. In this case, in a method of directly sticking the sensor pad on the patient using adhesive, a burden on the patient is large, and attachment and detachment are not easy.

Accordingly, an object of the present disclosure is to provide a probe unit easily attached and detached with low load.

Solution to Problem

A probe unit according to the present disclosure is a probe unit used to measure hemoglobin dynamics inside a subject, and includes a main body having flexibility, a first probe attached to the main body and having a first face from which a first light emitting portion configured to irradiate the subject with light is exposed, a second probe attached to the main body to face the first probe and having a second face from which a first light incidence portion configured to detect light propagated inside the subject is exposed, a first light shielding member having light shielding properties, containing an elastic material, and attached to the first face to surround an emission axis of the first light emitting portion, and a second light shielding member having light shielding properties, containing an elastic material, and attached to the second face to surround an incidence axis of the first light incidence portion.

In this probe unit, the first probe and the second probe are attached to the main body having flexibility so that the second probe, from which the first light incidence portion for detecting the light propagated inside the subject is exposed, faces the first probe, from which the first light emitting portion for irradiating the subject with the light is exposed.

For this reason, when measuring the hemoglobin dynamics inside the subject, if the subject is sandwiched between the first probe and the second probe while the distance between the first probe and the second probe is enlarged by bending the main body, the probe unit can be easily attached to the subject (easily attached and detached) by releasing bending of the main body. In addition, in this probe unit, the first light shielding member is arranged on the first face of the first probe to surround the emission axis of the first light emitting portion, and the second light shielding member is arranged on the second face of the second probe to surround the incidence axis of the first light incidence portion. For this reason, when the probe unit is attached to the subject, the first light shielding member and the second light shielding member containing an elastic material come into contact with the subject, thereby suppressing at least only the first probe and the second probe from contacting the subject. As a result, compared to the case where only the first probe and the second probe contact the subject, the load on the subject is reduced. Note that, for example, when the second probe does not contact the subject, there is concern that external light not subjected to detection may enter the first light incidence portion through a space created between the first light incidence portion and the subject. On the other hand, in the probe unit, when the probe unit is attached to the subject, the first light shielding member and the subject form a light shielding space around the first light emitting portion, and the second light shielding member and the subject form a light shielding space around the first light incidence portion. Therefore, incidence of light not subjected to detection is suppressed.

In the probe unit according to the present disclosure, each of the first probe and the second probe may be rotatably provided with respect to the main body. In this case, angles of the first probe and the second probe can be adjusted according to the shape or size of the subject. In this way, it is possible to appropriately set an incidence angle of light from the first probe to the subject and an incidence angle of light from the subject to the second probe.

In the probe unit according to the present disclosure, the first face of the first probe may further expose a second light incidence portion configured to detect light propagated inside the subject, the second face of the second probe may further expose a second light emitting portion configured to irradiate the subject with light, the first light shielding member may be attached to the first face to surround the emission axis of the first light emitting portion and an incidence axis of the second light incidence portion, and the second light shielding member may be attached to the second face to surround the incidence axis of the first light incidence portion and an emission axis of the second light emitting portion. In this case, two-channel measurement may be performed using the first probe and the second probe.

In the probe unit according to the present disclosure, the first light shielding member may include a first portion interposed between the first light emitting portion and the second light incidence portion of the first probe, and the second light shielding member may include a second portion interposed between the first light incidence portion and the second light emitting portion of the second probe. In this case, the light emitted from the first light emitting portion can be prevented from reflecting off the surface of the subject and directly entering the second light incidence portion. In addition, the light emitted from the second light emitting portion can be prevented from reflecting off the surface of the subject and entering the first light incidence portion. Therefore, incidence of light not subjected to detection is suppressed.

The probe unit according to the present disclosure may further include a shape memory member, wherein the main body may include a first support configured to support the first probe, a second support configured to support the second probe, and a coupling portion configured to couple the first support and the second support, and the shape memory member may be provided in the coupling portion. In this case, the first probe can be supported by the first support, and the second probe can be supported by the second support. In addition, the shape memory member can maintain the shape of the coupling portion.

In the probe unit according to the present disclosure, the main body may include a plurality of layer members laminated to each other, and a fixing member configured to detachably fix the plurality of layer members to each other. In this case, a freedom of configuration of the main body can be increased by combining the plurality of layer members detachably fixed to each other.

In the probe unit according to the present disclosure, the first probe and the second probe may each include an optical fiber, and the main body may include a fiber holding portion through which the optical fiber is inserted and configured to hold the optical fiber. In this case, the optical fiber can be held by the fiber holding portion. In this way, positional shift of the optical fiber can be suppressed.

In the probe unit according to the present disclosure, the main body may be made of rubber sponge. In this case, elastic force of the main body can reduce a burden on the subject.

Advantageous Effects of Invention

According to the present disclosure, it is possible to provide a probe unit easily attached and detached with low load.

BRIEF DESCRIPTION OF DRAWINGS

FIG. 6(*a*) is a plan view illustrating the first probe illustrated in FIG. 2, and FIG. 6(*b*) is a perspective view illustrating the first probe illustrated in FIG. 2.

DESCRIPTION OF EMBODIMENTS

Figure 1:
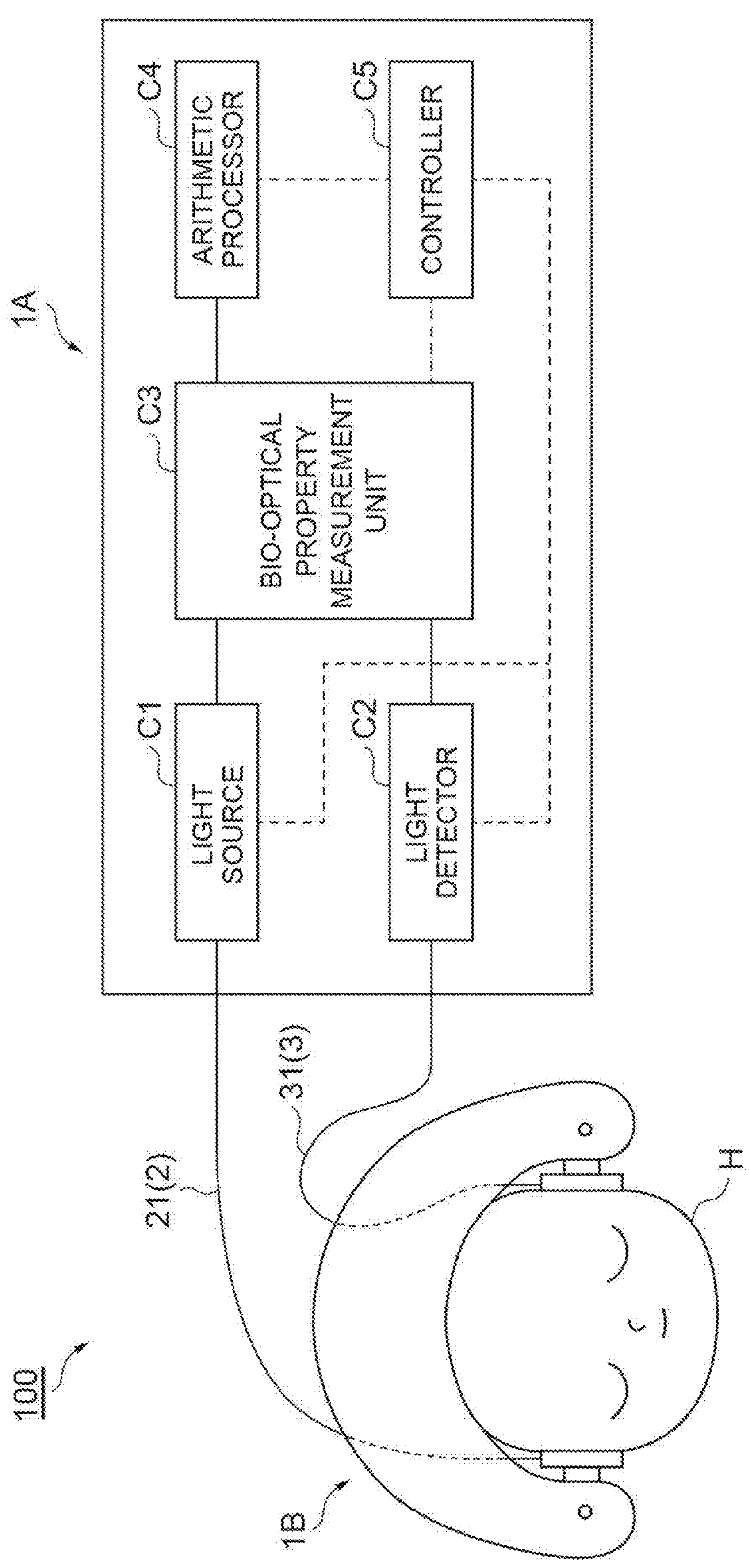
FIG. 1 is a schematic diagram illustrating a biometric apparatus according to a first embodiment.

Hereinafter, embodiments of a probe unit will be described with reference to the drawings. Note that, in the description of the drawings, the same elements or corresponding elements are denoted by the same reference numerals, and redundant description may be omitted.

First Embodiment

FIG. 1 is a schematic diagram illustrating a biometric apparatus according to a first embodiment. As illustrated in FIG. 1, the biometric apparatus 100 includes a bio-optical property measurement device 1A and a probe device 1B. Such a biometric apparatus 100 noninvasively measures substances in a living body using near-infrared spectroscopy, and is configured to irradiate a measurement target site (for example, deep brain) of a subject H with light from the probe device 1B while the probe device 1B is attached to the subject H, and detect light emitted from the subject H using the probe device 1B, so that a measurement result of an optical property (for example, light absorption property) of the measurement target site of the subject H is obtained by the bio-optical property measurement device 1A.

As an example, the biometric apparatus 100 is an apparatus for measuring a blood flow of the subject H, and can measure hemoglobin dynamics (for example, oxygenated hemoglobin, deoxygenated hemoglobin, and tissue oxygen saturation) in the subject H from the amount of attenuation and temporal diffusion of light by irradiating the subject H with inspection light of two or more near-infrared wavelengths (for example, wavelengths of 700 nm to 1200 nm) that is highly permeable to the living body, and detecting light transmitted through the subject H. The subject H is any living body, and is a human child (preterm infant) as an example.

The bio-optical property measurement device 1A measures an optical property of the living body, that is, a light absorption property of biological tissue, based on, for example, a time resolution measurement method, a phase difference measurement method, or a CW method. The bio-optical property measurement device 1A includes a light source C1, a light detector C2, a bio-optical property measurement unit C3, an arithmetic processor C4, and a controller C5.

The light source C1 generates different light depending on the measurement method. For example, the light source C1 generates pulsed light in the case of the time resolution measurement method, generates light modulated into a sine wave in the case of the phase difference measurement method, generates continuous light in the case of the CW method, and generates light at a plurality of wavelengths in some cases. Examples of the light source C1 include various light sources such as a light-emitting diode, a laser diode, and various pulse diodes. Further, light output from the light source C1 is input to an irradiation unit 2 (described later) connected to the light source C1, and the subject H is irradiated with the light.

The light detector C2 is connected to a detection unit 3 (described later) and is used to detect light output from the detection unit 3. The light detector C2 is connected to the bio-optical property measurement unit C3, and outputs a light detection signal indicating light intensity of detected light to the bio-optical property measurement unit C3. In addition to a photomultiplier tube (PMT), various devices such as a photodiode, an avalanche photodiode, a PIN photodiode, and a multi-pixel photon counter (MPPC) can be used as the light detector C2.

In addition, the light detector C2 may have a spectral sensitivity characteristic capable of sufficiently detecting a wavelength of light irradiated from the light source C1. In particular, when scattered light transmitted through a deep brain of the subject or fluorescence emitted from the inside of the brain is weak, a high-sensitivity or high-gain light detector may be used.

In the bio-optical property measurement unit C3, the light absorption property of the biological tissue is determined from changes in intensity or waveform of probe light within the subject. Data of the determined light absorption property is sent to the arithmetic processor C4. In the arithmetic processor C4, oxygenated hemoglobin concentration $C_{Hb}$ and deoxygenated hemoglobin concentration $C_{HbO2}$ in the brain of the subject can be determined by solving simultaneous equations of the following Example (1) for each wavelength of the light source C1. In the following Equation (1), $\mu_a$ denotes an absorption coefficient, ε denotes an extinction coefficient, and C denotes concentration.

$$\mu_{a,\lambda}=\varepsilon_{Hb02,\lambda}C_{Hbo2}+\varepsilon_{Hb,\lambda}C_{Hb} \quad (1)$$

Further, the arithmetic processor C4 derives the tissue oxygen saturation $SO_2$ from the determined oxygenated hemoglobin concentration and deoxygenated hemoglobin concentration. Meanwhile, controller C5 controls the light source C1, the light detector C2, the bio-optical property measurement unit C3, and the arithmetic processor C4.

Here, in a preterm infant, intracranial hemorrhage is an important problem in management of an acute stage. In the preterm infant, bleeding is mostly from upper and lower germinal layers surrounded by immature tissue. The preterm infant has immature cerebral vascular autoregulation and is susceptible to intraventricular hemorrhage due to changes in blood pressure affecting cerebral blood perfusion. Therefore, since hemoglobin dynamics changes in response to intraventricular hemorrhage, it is desirable to frequently measure hemoglobin dynamics in the subject H using the biometric apparatus. Therefore, it is desirable to facilitate attachment and detachment of the probe device.

Meanwhile, skin of the preterm infant is functionally and structurally immature, so that 2 to 3 layers are formed under 30 weeks of gestation and no layer is formed under 24 weeks of gestation. In addition, management of the preterm infant requires minimizing contact time of the probe device to subject H to minimize respiratory and hemodynamic fluctuations. That is, it is desirable to also reduce a load on the subject H caused by attaching the probe device to the subject H. In response thereto, the biometric apparatus 100 according to the present embodiment has a unique configuration to at least solve these problems. Subsequently, details of each part of the probe device 1B will be described.

Figure 2:
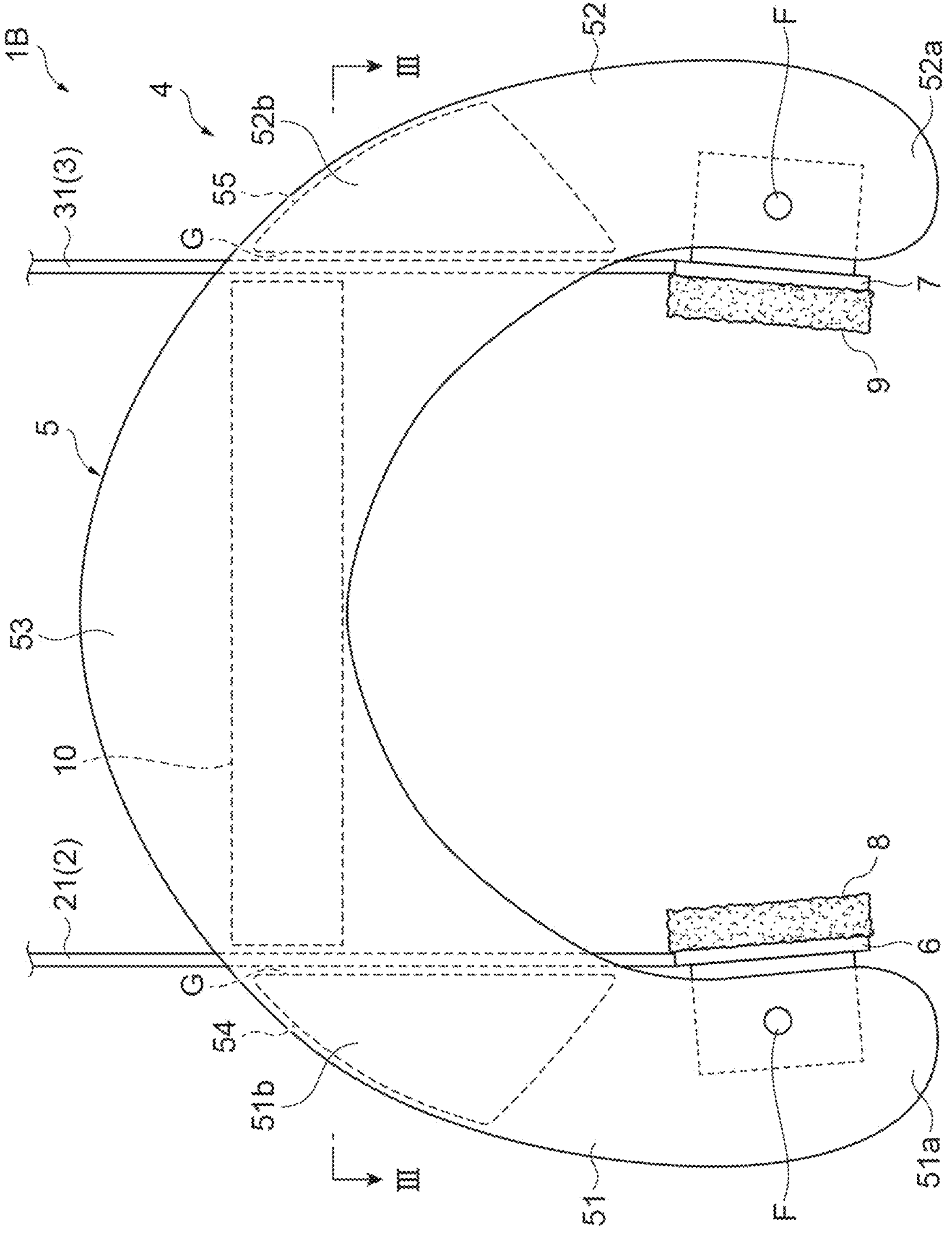
FIG. 2 is a schematic plan view of a probe device illustrated in FIG. 1.
Figure 3:
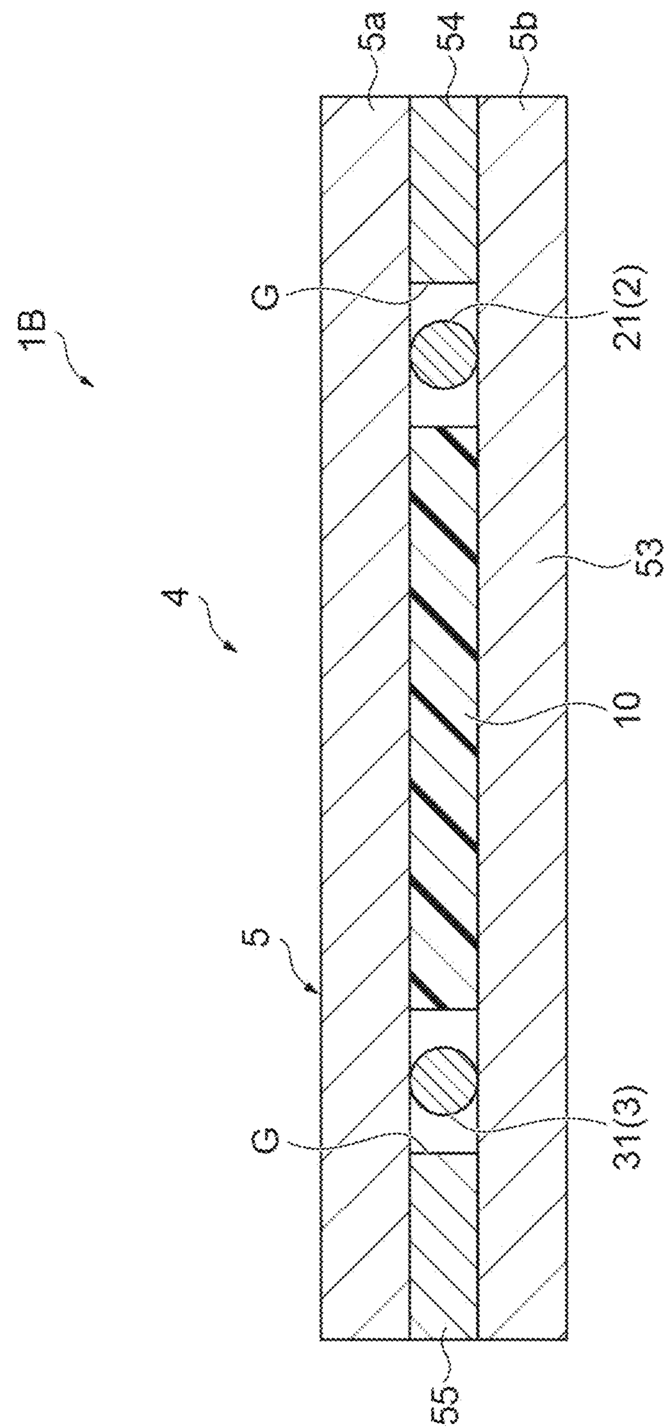
FIG. 3 is a cross-sectional view taken along the line III-III in FIG. 2.

FIG. 2 is a schematic plan view of the probe device illustrated in FIG. 1. FIG. 3 is a cross-sectional view taken along the line III-III in FIG. 2. As illustrated in FIGS. 1 to 3, the probe device 1B includes a probe unit 4 having the irradiation unit 2 and the detection unit 3. The irradiation unit 2 irradiates the subject H with light. An input end of the irradiation unit 2 is connected to the light source C1, and an output end of the irradiation unit 2 is held by the probe unit 4. While the probe device 1B is attached to the subject H, the irradiation unit 2 can irradiate the subject H with light, which is supplied from the light source C1, from the output end.

The detection unit 3 is used to detect light propagated inside the subject H. An output end of the detection unit 3 is connected to the light detector C2, and an input end of the detection unit 3 is held by the probe unit 4. While the probe device 1B is attached to the subject H, the detection unit 3 can detect light propagated inside the subject H from the input end, and output the detected light to the light detector C2.

As described above, the probe unit 4 has the irradiation unit 2 and the detection unit 3 (hereinafter may be simply referred to as "irradiation/detection unit"). As illustrated in FIG. 1, the probe unit 4 is arranged to sandwich the subject H therein. As illustrated in FIG. 2, the probe unit 4 includes a main body 5, a first probe 6 having the irradiation unit 2, a second probe 7 having the detection unit 3, a first light shielding member 8, a second light shielding member 9, and a shape memory member 10.

The main body 5 is a portion that forms a base of the probe unit 4. In the present embodiment, the main body 5 has an approximately U shape as a whole. For example, the main body 5 is made of rubber sponge, and has flexibility. The main body 5 has a first support 51, a second support 52, and a coupling portion 53.

As a constituent material for the main body 5, various materials such as natural rubber (NR), chloroprene rubber (CR), ethylene propylene diene rubber (EPDM), nitrile rubber (NBR), silicon rubber (Si), and styrene-butadiene rubber (SBR) may be used. In addition, the main body 5 may be made of an open-cell sponge, a fluororubber sponge, a polyurethane rubber sponge, etc. In addition, the main body 5 may be made of polyurethane foam or ethylene-vinyl acetate (polyethylene/EVA) foam. In addition, when the main body 5 is modeled by a 3D printer, a so-called rubber-like resin may be used as the constituent material of the main body 5. In this way, the material of the main body 5 can be selected from materials available in the 3D printer.

The first support 51 and the second support 52 are arranged to extend substantially parallel to each other to have a long length along one direction. The first support 51 has one end 51*a* and the other end 51*b* in a longitudinal direction. The second support 52 has one end 52*a* and the other end 52*b* in the longitudinal direction.

The coupling portion 53 couples the first support 51 and the second support 52 to each other. More specifically, the coupling portion 53 extends to have a long length along a direction intersecting the longitudinal direction of the first support 51 and the second support 52, and connects the other end 51*b* of the first support 51 and the other end 52*b* of the second support 52 to each other. In this way, the first support 51, the second support 52, and the coupling portion 53 are integrated to form the main body 5 in a U shape as a whole. Note that the first support 51, the second support 52, and the coupling portion 53 are curved to form one arc as a whole (along the head, which is one measurement target site of the subject H).

The first probe 6 is attached to the one end 51*a* of the first support 51. In other words, the first support 51 supports the first probe 6 by the first probe 6 attached thereto at the one end 51*a*. The second probe 7 is attached to the one end 52*a* of the second support 52. In other words, the second support 52 supports the second probe 7 by the second probe 7 attached thereto at the one end 52*a*.

The one end 51*a* of the first support 51 faces the one end 52*a* of the second support 52 along a longitudinal direction of the coupling portion 53. Therefore, the first probe 6 and the second probe 7 are arranged to face each other. In addition, fasteners F used to attach the first probe 6 and the second probe 7 are inserted through the one end 51*a* of the first support 51 and the one end 52*a* of the second support 52, respectively. Each of the fastener F is, for example, a screw made of resin.

The shape memory member 10 is provided in the coupling portion 53. The shape memory member 10 has, for example, an elongated rectangular shape extending along the longitudinal direction of the coupling portion 53. The shape memory member 10 is a member for retaining the shape of the coupling portion 53 (that is, the main body 5). The shape memory member 10 is made of, for example, shape memory resin. The shape memory member 10 is embedded in the coupling portion 53. In the present embodiment, the elastic modulus of the shape memory member 10 is higher than the elastic modulus of the main body 5.

More specifically, the main body 5 includes a plurality of (here, two) layer members 5*a* and 5*b* laminated to each other, and the shape memory member 10 is embedded in the coupling portion 53 by being interposed between the layer members 5*a* and 5*b*. The layer member 5*a* and the layer member 5*b* have substantially the same shape. Outer shapes of the layer members 5*a* and 5*b* define an outer shape of the main body 5 (match the outer shape of the main body 5) when viewed in a stacking direction of the layer members 5*a* and 5*b*.

In addition, the main body 5 includes fixing members 54 and 55 for detachably fixing the plurality of layer members 5*a* and 5*b* to each other. For example, the fixing members 54 and 55 are hook-and-loop fasteners. When the fixing members 54 and 55 are the hook-and-loop fasteners, the fixing members 54 and 55 can be configured so that the plurality of layer members 5*a* and 5*b* can be attached to and detached from each other, and the bending strength of the main body 5 can be improved. The layer members 5*a* and 5*b* are glued together by the fixing members 54 and 55 arranged between the layer members 5*a* and 5*b*. The fixing member 54 is arranged at the other end 51*b* of the first support 51, and the fixing member 55 is arranged at the other end 52*b* of the second support 52.

Therefore, the fixing member 54 and the fixing member 55 are separated from each other with the coupling portion 53 and the shape memory member 10 interposed therebetween. Further, the shape memory member 10 is separated from each of the fixing members 54 and 55. As a result, gaps G (fiber holding portions) are formed between the fixing member 54 and the shape memory member 10 and between the fixing member 55 and the shape memory member 10, respectively.

An optical fiber 21 of the irradiation unit 2 is inserted through the gap G formed between the fixing member 54 and the shape memory member 10. The layer member 5*a* and the layer member 5*b* are fixed to each other while the optical fiber 21 is inserted through the gap G, and thus the optical fiber 21 is held in the main body 5 by being sandwiched between the layer members 5*a* and 5*b*, the fixing member 54, and the shape memory member 10. An optical fiber 31 of the detection unit 3 is inserted through the gap G formed between the fixing member 55 and the shape memory member 10. As the optical fiber 31, the same one as the optical fiber 21 may be used, or a different one may be used. The layer member 5*a* and the layer member 5*b* are fixed to each other while the optical fiber 31 is inserted through the gap G, and thus the optical fiber 31 is held by being sandwiched between the layer members 5*a* and 5*b*, the fixing member 55, and the shape memory member 10. In this way, the main body 5 has the gaps G as the fiber holding portions for holding the optical fiber 21 of the irradiation unit 2 and the optical fiber 31 of the detection unit 3.

The first probe 6 is attached to and supported by the one end 51*a* of the first support 51. The first probe 6 is rotatably provided with respect to the main body 5 (first support 51). Here, the first probe 6 is attached to the main body 5 (first support 51) by the fastener F inserted through the first probe 6 together with the first support 51. In this way, the first probe 6 is rotatable with respect to the main body 5 using the fastener F as a rotation axis.

The second probe 7 is attached to and supported by the one end 52*a* of the second support 52 to face the first probe 6. The second probe 7 is rotatably provided with respect to the main body 5 (second support 52). The second probe 7 is attached to the main body 5 (second support 52) by the fastener F inserted through the second probe 7 together with the second support 52. In this way, the second probe 7 is rotatable with respect to the main body 5 using the fastener F as a rotation axis.

The first light shielding member 8 is a cushioning member interposed between the subject H and the first probe 6 while the subject H is attached to the probe device 1B. The first light shielding member 8 is detachably attached to the first probe 6 by an adhesive member such as double-sided tape. In addition, the second light shielding member 9 is a cushioning member interposed between the subject H and the second probe 7 while the subject H is attached with the probe device 1B. The second light shielding member 9 is detachably attached to the second probe 7 by an adhesive member such as double-sided tape. Details of the first light shielding member 8 and the second light shielding member 9 will be described later.

As described above, for example, each of the fasteners F for attaching the first probe 6 and the second probe 7 to the main body 5 is a resin screw and can be configured without metal. Furthermore, other portions of the probe device 1B (for example, the irradiation/detection unit itself and each part of the probe unit 4) can be also configured without metal as a constituent material. In this case, the probe device 1B can be used for simultaneous measurement with MRI (magnetic resonance imaging).

Subsequently, the first probe 6, the second probe 7, the first light shielding member 8, the second light shielding member 9, and peripheral structures thereof will be described with reference to FIGS. 4 to 7. First, a configuration on the first probe 6 side will be described.

Figure 4:
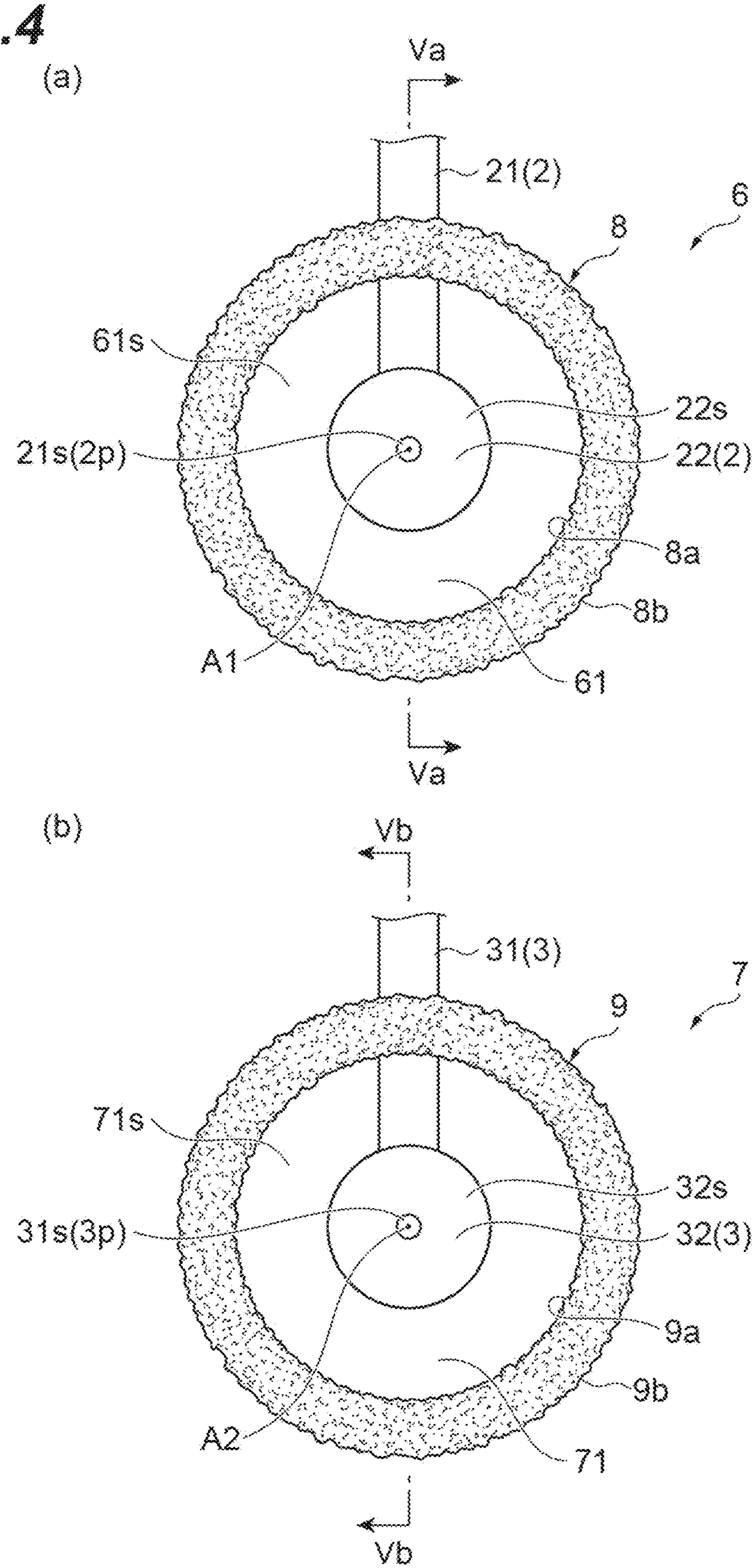
FIG. 4(*a*) is a schematic plan view of a first probe illustrated in FIG. 2, and FIG. 4(*b*) is a schematic plan view of a second probe illustrated in FIG. 2.
Figure 5:
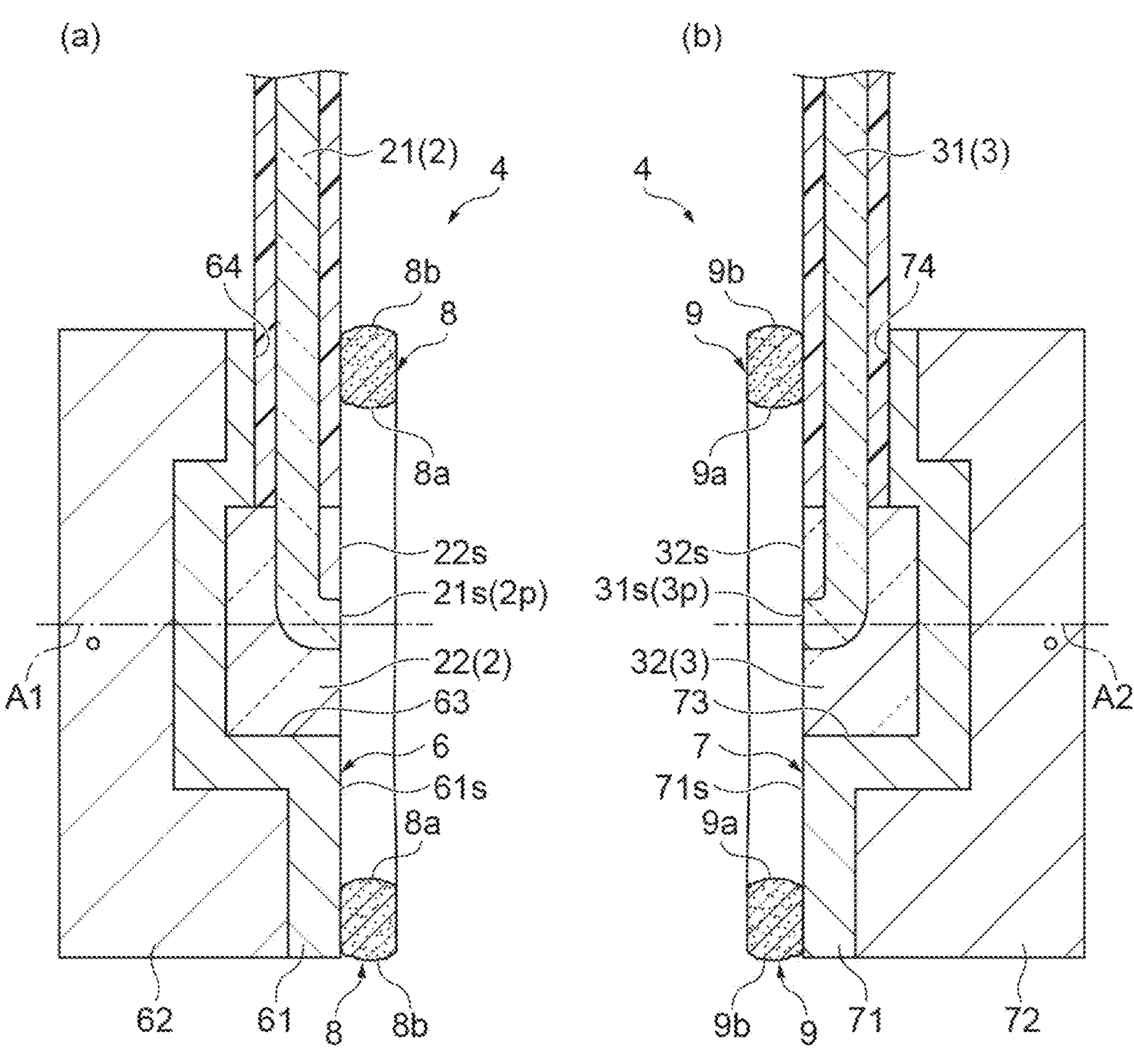
FIG. 5(*a*) is a cross-sectional view taken along the line Va-Va in FIG. 4, and FIG. 5(*b*) is a cross-sectional view taken along the line Vb-Vb in FIG. 4.
Figure 7:
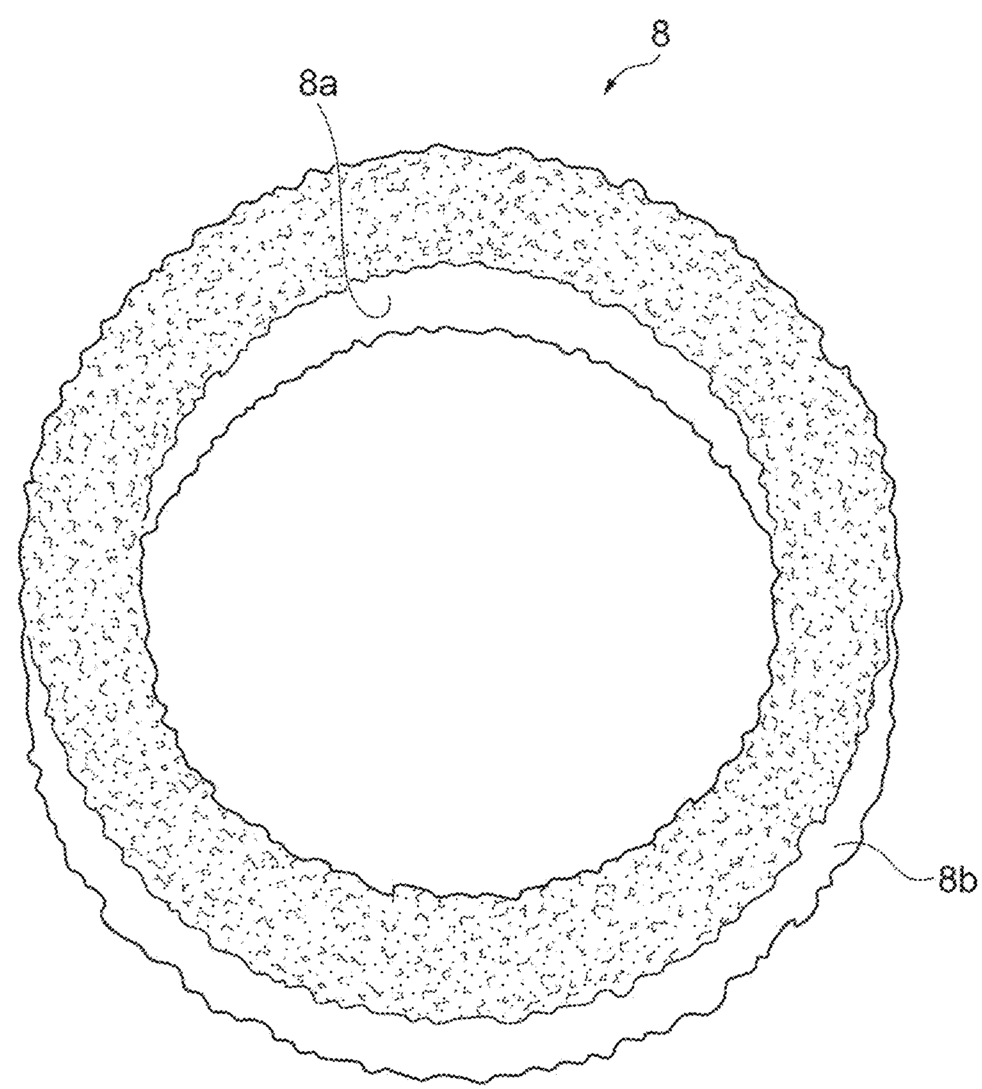
FIG. 7 is a perspective view illustrating a first light shielding member illustrated in FIG. 2.

FIG. 4(*a*) is a schematic plan view of the first probe illustrated in FIG. 2, and FIG. 4(*b*) is a schematic plan view of the second probe illustrated in FIG. 2. FIG. 5(*a*) is a cross-sectional view taken along the line Va-Va in FIG. 4, and FIG. 5(*b*) is a cross-sectional view taken along the line Vb-Vb in FIG. 4. FIG. 6(*a*) is a plan view illustrating the first probe illustrated in FIG. 2, and FIG. 6(*b*) is a perspective view illustrating the first probe illustrated in FIG. 2. FIG. 7 is a perspective view illustrating the first light shielding member illustrated in FIG. 2. Note that, in an example illustrated in FIG. 6, the irradiation unit 2 is omitted among components of the first probe.

As illustrated in FIG. 4(*a*) and FIG. 5(*a*), the irradiation unit 2 includes the optical fiber 21 and a fitting portion 22 provided on the optical fiber 21. The optical fiber 21 is exposed from coating at a part of the irradiation unit 2 on the output end side, and the fitting portion 22 is provided to cover a portion of the optical fiber 21 exposed from the coating. For example, the fitting portion 22 is made of resin. The fitting portion 22 has an end face 22*s*. The optical fiber 21 is inserted into the fitting portion 22 from a side surface different from the end face 22*s* of the fitting portion 22 and reaches the end face 22*s*. An end face 21*s* of the optical fiber 21 is exposed to the end face 22*s* of the fitting portion 22. Here, the end face 21*s* of the optical fiber 21 is flush with the end face 22*s* of the fitting portion 22. Light from the light source C1 is emitted from the end face 21*s* of the optical fiber 21. Therefore, the end face 21*s* of the optical fiber 21 is included in a light emitting portion 2*p* (first light emitting portion) of the irradiation unit 2. The optical fiber 21 emits light along an emission axis A1 of the light emitting portion 2*p*.

As illustrated in FIG. 5(*a*), the first probe 6 has a holding portion 61 and an attaching portion 62. The holding portion 61 is a portion for holding the irradiation unit 2. The attaching portion 62 is a portion for attaching the first probe 6 to the main body 5. The first probe 6 is attached to the main body 5 by the attaching portion 62 arranged between the layer member 5*a* and the layer member 5*b* of the main body 5 and the fastener F inserted through the attaching portion 62 together with the main body 5 (first support 51). The holding portion 61 has a first surface 61*s* (first face) facing the opposite side from a portion (first support 51) of the main body 5 to which the first probe 6 is attached while the first probe 6 is attached to the main body 5 via the attaching portion 62.

The holding portion 61 has a substantially circular shape when viewed in a first direction intersecting the first surface 61*s*. That is, here, the first surface 61*s* has a circular shape. A recess 63 and a groove 64 open to the first surface 61*s* are formed on the holding portion 61. The recess 63 is provided here substantially at a center of the first surface 61*s*, and the groove 64 extends from the recess 63 to an outer edge of the holding portion 61. A shape of the recess 63 is substantially the same as an outer shape of the fitting portion 22 of the irradiation unit 2. The irradiation unit 2 is held in the holding portion 61 by fitting the fitting portion 22 into the recess 63. At this time, the end face 21*s* of the optical fiber 21 is exposed on the first surface 61*s*. As an example, the first surface 61*s* and the end face 21*s* are flush with each other.

In this way, the first probe 6 is attached to the main body 5 and has the first surface 61*s* facing the opposite side from the main body 5, and the light emitting portion 2*p* of the irradiation unit 2 (the end face 21*s* of the optical fiber 21) for irradiating the subject H with light is exposed on the first surface 61*s*. Note that the optical fiber 21 of the irradiation unit 2 is arranged in the groove 64.

As illustrated in FIG. 4(*a*) and FIG. 7, the first light shielding member 8 has an outer shape following an outer shape of the first surface 61*s* of the holding portion 61. As an example, the first light shielding member 8 has an annular shape. The first light shielding member 8 has an inner peripheral face 8*a* and an outer peripheral face 8*b*. The first light shielding member 8 has light shielding properties and contains an elastic material. Here, the first light shielding member 8 is made of an elastic material having light shielding properties. Examples of a material of the first light shielding member 8 include natural rubber (NR), chloroprene rubber (CR), ethylene propylene diene rubber (EPDM), nitrile rubber (NBR), silicon rubber (Si), and styrene-butadiene rubber (SBR), and the first light shielding member 8 may be formed in a spongy shape using the material. As the material of the first light shielding member 8, the same material as that of the main body 5 can be used. A thickness of the first light shielding member 8 is generally constant in a circumferential direction.

The first light shielding member 8 is attached to the first surface 61*s* of the holding portion 61 of the first probe 6 to surround the light emitting portion 2*p* of the irradiation unit 2 when viewed in the first direction intersecting the first surface 61*s*. That is, the first light shielding member 8 is attached to the first surface 61*s* to surround the emission axis A1 of the light emitting portion 2*p*. More specifically, as illustrated in FIG. 4(*a*) and FIG. 5(*a*), the first light shielding member 8 is attached to the first surface 61*s* so that the outer peripheral face 8*b* is located at an outer edge of the first surface 61*s*, and the light emitting portion 2*p* of the irradiation unit 2 is located inside the inner peripheral face 8*a* when viewed in the first direction. In the present embodiment, an outer diameter of the first light shielding member 8 is substantially equal to an outer diameter of the first surface 61*s*. In addition, an inner diameter of the first light shielding member 8 is larger than an outer diameter of the recess 63.

Next, a configuration on the second probe 7 side will be described. Note that, even though the second probe 7 has the same configuration as that of the first probe 6 described above, the same description as that of the first probe 6 will be given. As illustrated in FIG. 4(*b*) and FIG. 5(*b*), the detection unit 3 includes the optical fiber 31 and a fitting portion 32 provided on the optical fiber 31. The optical fiber 31 is exposed from coating at a part of the detection unit 3 on the input end side, and the fitting portion 32 is provided to cover a portion of the optical fiber 31 exposed from the coating. For example, the fitting portion 32 is made of resin. The fitting portion 32 has an end face 32*s*. The optical fiber 31 is inserted into the fitting portion 32 from a side surface different from the end face 32*s* of the fitting portion 32 and reaches the end face 32*s*. An end face 31*s* of the optical fiber 31 is exposed to the end face 32*s* of the fitting portion 32. Here, the end face 31*s* of the optical fiber 31 is flush with the end face 32*s* of the fitting portion 32. Light from the subject H enters from the end face 31*s* of the optical fiber 31. Therefore, the end face 31*s* of the optical fiber 31 is included in a light incidence portion 3*p* (first light incidence portion) of the detection unit 3. Light enters the optical fiber 31 along an incidence axis A2 of the light incidence portion 3*p*.

As illustrated in FIG. 5(*b*), the second probe 7 has a holding portion 71 and an attaching portion 72. The holding portion 71 is a portion for holding the detection unit 3. The attaching portion 72 is a portion for attaching the second probe 7 to the main body 5. The second probe 7 is attached to the main body 5 by the attaching portion 72 arranged between the layer member 5*a* and the layer member 5*b* of the main body 5 and the fastener F inserted through the attaching portion 72 together with the main body 5 (second support 52). The holding portion 71 has a second surface 71*s* (second face) facing the opposite side from a portion (second support 52) of the main body 5 to which the second probe 7 is attached while the second probe 7 is attached to the main body 5 via the attaching portion 72.

The holding portion 71 has a substantially circular shape when viewed in a second direction intersecting the second surface 71*s*. That is, here, the second surface 71*s* has a circular shape. A recess 73 and a groove 74 open to the second surface 71*s* are formed on the holding portion 71. The recess 73 is provided here substantially at a center of the second surface 71*s*, and the groove 74 extends from the recess 73 to an outer edge of the holding portion 71. A shape of the recess 73 is substantially the same as an outer shape of the fitting portion 32 of the detection unit 3. The detection unit 3 is held in the holding portion 71 by fitting the fitting portion 32 into the recess 73. At this time, the end face 31*s* of the optical fiber 31 is exposed on the second surface 71*s*. As an example, the second surface 71*s* and the end face 31*s* are flush with each other.

In this way, the second probe 7 is attached to the main body 5 to face the first probe 6 and has the second surface 71*s* facing the opposite side from the main body 5, and the light incidence portion 3*p* of the detection unit 3 (the end face 31*s* of the optical fiber 31) for detecting light propagated inside the subject H is exposed on the second surface 71*s*. Note that the optical fiber 31 of the detection unit 3 is arranged in the groove 74.

As illustrated in FIG. 4(*b*) and FIG. 7, the second light shielding member 9 has an outer shape following an outer shape of the second surface 71*s* of the holding portion 71. As an example, the second light shielding member 9 has an annular shape. The second light shielding member 9 has an inner peripheral face 9*a* and an outer peripheral face 9*b*. The second light shielding member 9 has light shielding properties and contains an elastic material. Here, the second light shielding member 9 is made of an elastic material having light shielding properties. Examples of a material of the second light shielding member 9 include natural rubber (NR), chloroprene rubber (CR), ethylene propylene diene rubber (EPDM), nitrile rubber (NBR), silicon rubber (Si), and styrene-butadiene rubber (SBR), and the second light shielding member 9 may be formed in a spongy shape using the material. As the material of the second light shielding member 9, the same material as that of the main body 5 can be used. A thickness of the second light shielding member 9 is generally constant in a circumferential direction.

The second light shielding member 9 is attached to the second surface 71*s* of the holding portion 71 of the second probe 7 to surround the light incidence portion 3*p* of the detection unit 3 when viewed in the second direction intersecting the second surface 71*s*. That is, the second light shielding member 9 is attached to the second surface 71*s* to surround the incidence axis A2 of the light incidence portion 3*p*. More specifically, as illustrated in FIG. 4(*b*) and FIG. 5(*b*), the second light shielding member 9 is attached to the second surface 71*s* so that the outer peripheral face 9*b* is located at an outer edge of the second surface 71*s*, and the light incidence portion 3*p* of the detection unit 3 is located inside the inner peripheral face 9*a* when viewed in the second direction. In the present embodiment, an outer diameter of the second light shielding member 9 is substantially equal to an outer diameter of the second surface 71*s*. In addition, an inner diameter of the second light shielding member 9 is larger than an outer diameter of the recess 73.

Figure 8:
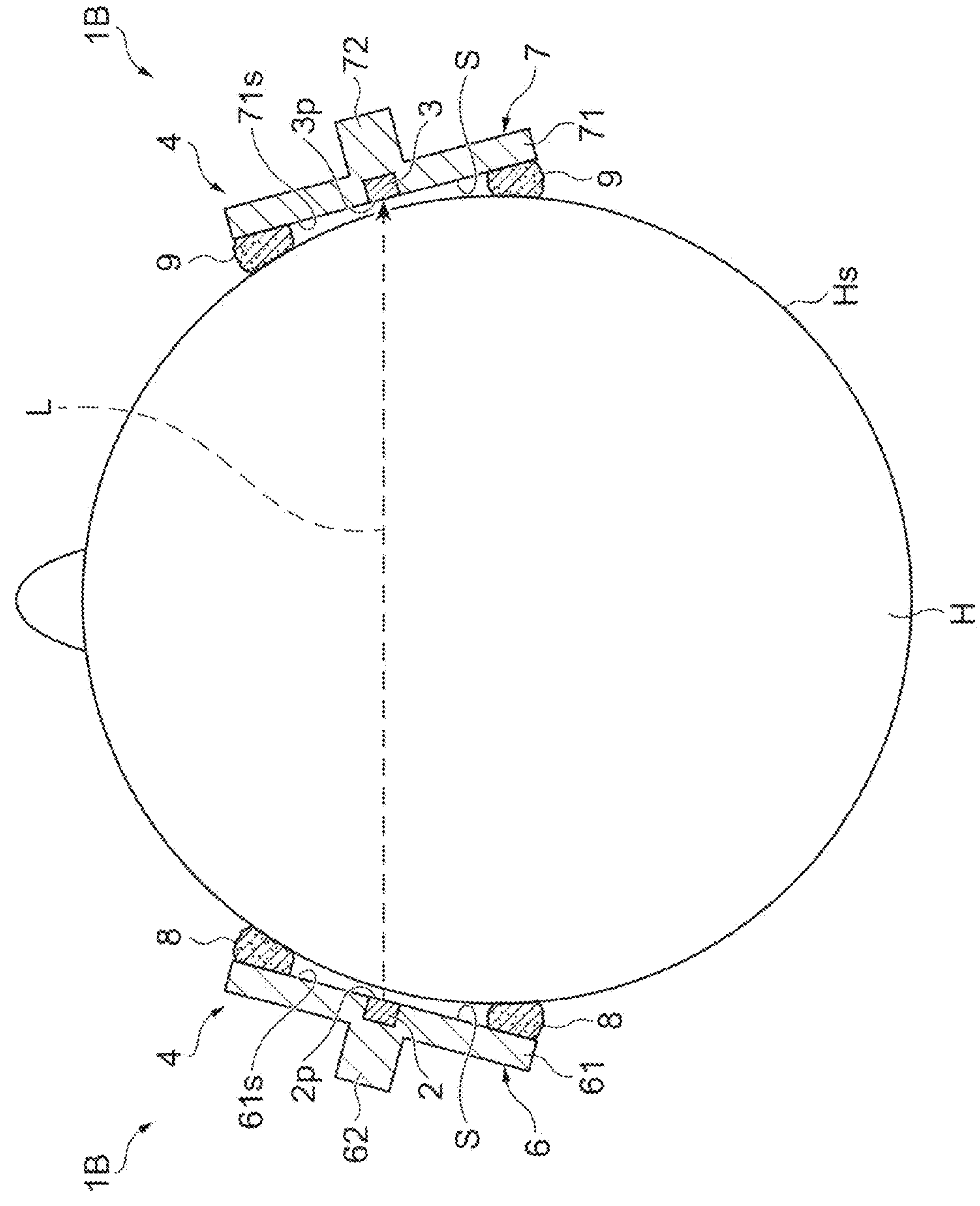
FIG. 8 is a diagram illustrating a state in which the probe device according to the first embodiment is attached to a subject.
Figure 9:
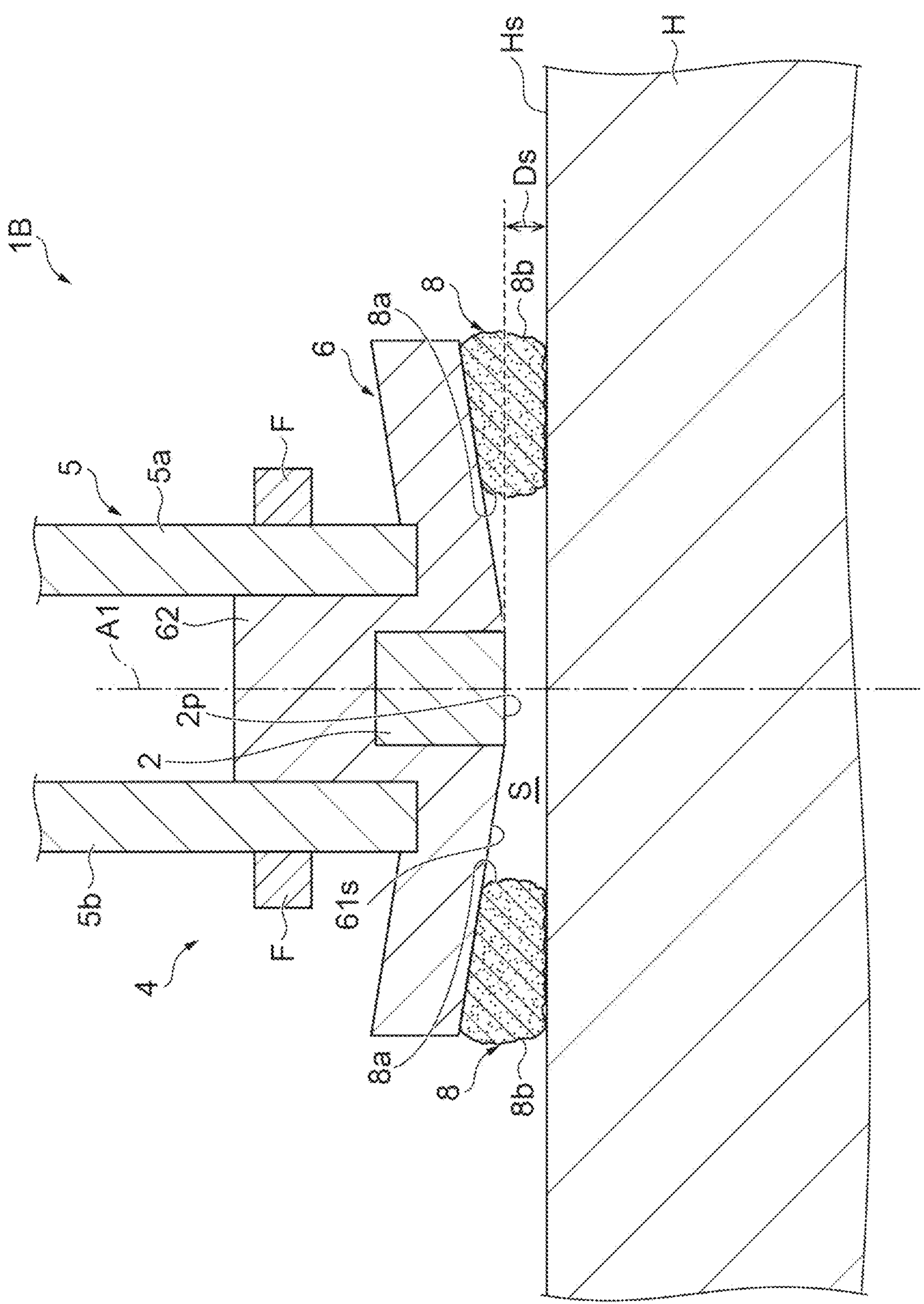
FIG. 9 is a schematic cross-sectional view enlarging and illustrating a part of FIG. 8.

Subsequently, a biometric method using the biometric apparatus 100 configured as described above will be described. FIG. 8 is a diagram illustrating a state in which the probe device according to the first embodiment is attached to the subject. FIG. 9 is a schematic cross-sectional view enlarging and illustrating a part of FIG. 8. In FIG. 9, only a configuration on the first probe 6 side is illustrated.

As illustrated in FIGS. 8 and 9, in this method, first, the probe device 1B is attached to the measurement target site (here, the head) of the subject H. As an example, the probe device 1B is attached such that the light emitting portion 2*p* of the irradiation unit 2 and the light incidence portion 3*p* of the detection unit 3 are located on right and left temples of the subject H. At this time, the subject H is positioned between the first probe 6 and the second probe 7 by bending the main body 5 to widen a distance between the first probe 6 and the second probe 7. In this state, bending of the main body 5 is released to reduce the distance between the first probe 6 and the second probe 7. In this way, the probe device 1B is attached to the subject H using elastic force of the main body 5. The first light shielding member 8 is attached to the first surface 61*s* of the first probe 6, and the second light shielding member 9 is attached to the second surface 71*s* of the second probe 7. Therefore, when the probe device 1B is attached to the subject H, at least the first light shielding member 8 and the second light shielding member 9 come into contact with the subject H.

That is, the first light shielding member 8 is interposed between the first probe 6 and the subject H, and the second light shielding member 9 is interposed between the second probe 7 and the subject H. Here, on the first probe 6 side, the first light shielding member 8 is in contact with the surface Hs of the subject H, and the first surface 61*s* of the first probe 6 and the light emitting portion 2*p* of the irradiation unit 2 are separated from the surface Hs of the subject H. In addition, on the second probe 7 side, the second light shielding member 9 is in contact with the surface Hs of the subject H, and the second surface 71*s* of the second probe 7 and the light incidence portion 3*p* of the detection unit 3 are separated from the surface Hs of the subject H. As an example, a distance Ds between the light emitting portion 2*p* of the irradiation unit 2 and the surface Hs of the subject H (and a distance between the light incidence portion 3*p* of the detection unit 3 and the surface Hs of the subject H) is about 1 mm.

In this way, here, the probe device 1B is in contact with the subject H only at the first light shielding member 8 and the second light shielding member 9. Such a contact state can be controlled by, for example, adjusting thicknesses of the first light shielding member 8 and the second light shielding member 9. That is, only the first light shielding member 8 and the second light shielding member 9 can be brought into contact with the subject H by relatively increasing the thicknesses of the first light shielding member 8 and the second light shielding member 9, whereas, in addition to the first light shielding member 8 and the second light shielding member 9, the light emitting portion 2*p* of the irradiation unit 2 and the light incidence portion 3*p* of the detection unit 3 can be also brought into contact with the subject H by relatively decreasing the thicknesses of the first light shielding member 8 and the second light shielding member 9.

Note that a size of the probe unit 4 can be selected in order to appropriately set force with which the probe device 1B sandwiches the subject H when the probe device 1B is attached to the subject H. That is, as an example, when a size of the measurement target site of the subject H is 4.5 cm to 5.5 cm, an S-D distance, which is a distance between the light emitting portion 2*p* and the light incidence portion 3*p* in a natural state, is set to about 4 cm, and when the size of the measurement target site of the subject H is 5.5 cm to 6.5 cm, the S-D distance is set to about 5 cm. Further, when the size of the measurement target site of the subject H is 6.5 cm to 7.5 cm, the probe device 1B can be attached to the subject H while increasing the S-D distance by about 1 cm while setting the S-D distance to about 6 cm. Note that the natural state is a state in which the subject H is not sandwiched and no external force is applied to the probe device 1B.

In the probe device 1B, by realizing the contact state described above, the first probe 6, the first light shielding member 8, and the subject H form a light shielding space S, which is shielded from external light, between the first probe 6 and the subject H. Similarly, the second probe 7, the second light shielding member 9, and the subject H form a light shielding space S, which is shielded from external light, between the second probe 7 and the subject H. Note that, as described above, the first probe 6 and the second probe 7 are rotatable with respect to the main body 5. Therefore, by rotating the first probe 6 and the second probe 7 when the probe device 1B is attached to the subject H, postures of the first probe 6 and the second probe 7 are adjusted to follow the shape of the subject H (the shape of the head).

Subsequently, while the probe device 1B is attached to the subject H as described above, light L is provided from the light source C1 to the irradiation unit 2 under the control of the controller C5 of the bio-optical property measurement device 1A. This light L is emitted from the light emitting portion 2*p* of the irradiation unit 2 of the first probe 6 to irradiate the subject H. Here, in the biometric apparatus 100, the time resolution measurement method is implemented to measure hemoglobin dynamics of the subject H. Therefore, here, a plurality of (for example, three) light rays L, which are pulsed light rays and have different wavelengths, are sequentially irradiated. The wavelengths of the light L are, for example, 760 nm, 800 nm, and 830 nm.

Then, the light L propagated inside the subject H is detected by the detection unit 3 of the second probe 7 and output to the light detector C2 of the bio-optical property measurement device 1A. Thereafter, based on this detection result (the amount of attenuation, temporal diffusion, etc. of the light L), the bio-optical property measurement unit C3 and the arithmetic processor C4 of the bio-optical property measurement device 1A derive oxygenated hemoglobin, deoxygenated hemoglobin, tissue oxygen saturation, etc. in a cranium of the subject H. In this way, in the present embodiment, the biometric apparatus 100 performs so-called transmission type measurement. In this transmission type measurement, since the light L propagated through a deep part of the subject H is detected, the hemoglobin dynamics in the deep part of the subject H can be measured.

As described above, in the probe unit 4, the first probe 6 and the second probe 7 are attached to the main body 5 having flexibility so that the second probe 7, from which the light incidence portion 3*p* for detecting the light L propagated inside the subject H is exposed, faces the first probe 6, from which the light emitting portion 2*p* for irradiating the subject H with the light L is exposed. For this reason, when measuring the hemoglobin dynamics inside the subject H, if the subject H is sandwiched between the first probe 6 and the second probe 7 while the distance between the first probe 6 and the second probe 7 is enlarged by bending the main body 5, the probe unit 4 (and the irradiation/detection unit) can be easily attached to the subject H (easily attached and detached) by releasing bending of the main body 5.

In addition, in the probe unit 4, the first light shielding member 8 is arranged on the first surface 61*s* of the first probe 6 to surround the emission axis A1 of the light emitting portion 2*p*, and the second light shielding member 9 is arranged on the second surface 71*s* of the second probe 7 to surround the incidence axis A2 of the light incidence portion 3*p*. For this reason, when the probe unit 4 is attached to the subject H, the first light shielding member 8 and the second light shielding member 9 containing an elastic material come into contact with the subject H, thereby suppressing at least only the first probe 6 and the second probe 7 from contacting the subject H. As a result, compared to the case where only the first probe 6 and the second probe 7 contact the subject H, the load on the subject H is reduced. Note that, for example, when the second probe 7 does not contact the subject H, there is concern that external light not subjected to detection may enter the light incidence portion 3*p* through a space created between the light incidence portion 3*p* of the detection unit 3 and the subject H. On the other hand, in the probe unit 4, when the probe unit 4 is attached to the subject H, the first light shielding member 8 and the subject H form a light shielding space S around the light emitting portion 2*p*, and the second light shielding member 9 and the subject H form a light shielding space S around the light incidence portion 3*p*. Therefore, incidence of light not subjected to detection is suppressed.

Further, in the probe unit 4, each of the first probe 6 and the second probe 7 is rotatably provided with respect to the main body 5. For this reason, angles of the first probe 6 and the second probe 7 can be adjusted according to the shape or size of the subject H. In this way, it is possible to appropriately set an incidence angle of light from the first probe 6 to the subject H and an incidence angle of light from the subject H to the second probe 7.

Further, the probe unit 4 includes the shape memory member 10, the main body 5 includes the first support 51 that supports the first probe 6, the second support 52 that supports the second probe 7, and the coupling portion 53 that couples the first support 51 and the second support 52, and the shape memory member 10 is provided in the coupling portion 53. For this reason, the first probe 6 can be supported by the first support 51, and the second probe 7 can be supported by the second support 52. In addition, the shape memory member 10 can maintain the shape of the coupling portion 53.

Further, in the probe unit 4, the main body 5 includes the plurality of layer members 5*a* and 5*b* laminated to each other, and the fixing members 54 and 55 for detachably fixing the plurality of layer members 5*a* and 5*b* to each other. For this reason, a freedom of configuration of the main body 5 can be increased by combining the plurality of layer members 5*a* and 5*b* detachably fixed to each other.

Further, in the probe unit 4, the first probe 6 and the second probe 7 include the optical fibers 21 and 31, respectively, and the main body 5 has the gaps G through which the optical fibers 21 and 31 are inserted and which hold the optical fibers 21 and 31. For this reason, the optical fibers 21 and 31 can be held by the gaps G. In this way, positional shift of the optical fibers 21 and 31 can be suppressed.

Further, in the probe unit 4, the main body 5 is made of rubber sponge. For this reason, elastic force of the main body 5 can reduce the burden on the subject H.

Note that the probe unit 4 can be configured not to contain metal as a constituent material. In this case, when the probe device 1B is attached to the subject H, a metal member can be inhibited from contacting the subject H. Moreover, according to such a configuration, measurement by MRI can be performed while the probe device 1B is attached.

Second Embodiment

Subsequently, a biometric apparatus 100 according to a second embodiment will be described with reference to FIGS. 10 and 11. The biometric apparatus 100 according to the second embodiment is different from the biometric apparatus 100 according to the first embodiment in that a probe device 1D is provided instead of the probe device 1B. In the probe device 1D, the probe unit 4 has two pairs of irradiation/detection units. More specifically, in the probe unit 4 according to the second embodiment, each of the first probe 6 and the second probe 7 has the irradiation unit 2 and the detection unit 3.

That is, here, the first probe 6 has another detection unit 3 for detecting the light L propagated inside the subject H. A light incidence portion 3*p* (second light incidence portion) of the other detection unit 3 is exposed on the first surface 61*s*. In addition, the second probe 7 has another irradiation unit 2 for irradiating the subject H with the light L. A light emitting portion 2*p* (second light emitting portion) of the other irradiation unit 2 is exposed on the second surface 71*s*. A mode of each irradiation/detection unit is the same as that in the first embodiment.

In addition, the first light shielding member 8 is attached to the first surface 61*s* to surround the light emitting portion 2*p* of the irradiation unit 2 and the light incidence portion 3*p* of the detection unit 3 when viewed in the first direction intersecting the first surface 61*s*, and the second light shielding member 9 is attached to the second surface 71*s* to surround the light incidence portion 3*p* of the detection unit 3 and the light emitting portion 2*p* of the irradiation unit 2 when viewed in the second direction intersecting the second surface 71*s*. That is, the first light shielding member 8 is attached to the first surface 61*s* to surround the emission axis A1 of the light emitting portion 2*p* of the irradiation unit 2 and the incidence axis A2 of the light incidence portion 3*p* of the detection unit 3, and the second light shielding member 9 is attached to the second surface 71*s* to surround the incidence axis A2 of the light incidence portion 3*p* of the detection unit 3 and the emission axis A1 of the light emitting portion 2*p* of the irradiation unit 2. That is, in the probe device 1D, one first light shielding member 8 and one second light shielding member 9 surround a light incidence/emission portion of the irradiation/detection unit.

Further, the first light shielding member 8 includes a portion (first portion) 8*p* interposed between the light emitting portion 2*p* of the irradiation unit 2 and the light incidence portion 3*p* of the detection unit 3 when viewed in the first direction, and the second light shielding member 9 includes a portion (second portion) 9*p* interposed between the light emitting portion 2*p* of the irradiation unit 2 and the light incidence portion 3*p* of the detection unit 3 when viewed in the second direction. The portion 8*p* is provided across mutually facing regions of the inner peripheral face 8*a* to pass between the light emitting portion 2*p* and the light incidence portion 3*p*. In addition, the portion 9*p* is provided across mutually facing regions of the inner peripheral face 9*a* to pass between the light emitting portion 2*p* and the light incidence portion 3*p*.

In this way, when the probe device 1D is attached to the subject H, light shielding spaces S1 and S2, which are separated from each other by the portion 8*p* or the portion 9*p* and are independent of each other, are formed around each of the light emitting portion 2*p* and the light incidence portion 3*p*.

Subsequently, a description will be given of a biometric method using the biometric apparatus 100 according to the second embodiment configured as described above. In this method, the probe device 1D described above is attached to the subject H. An attaching method is the same as that of the probe device 1B according to the first embodiment.

Subsequently, while the probe device 1D is attached to the subject H as described above, light L1 is provided from the light source C1 to the irradiation unit 2 of the first probe 6 and light L2 is supplied from the light source C1 to the irradiation unit 2 of the first second probe 7 under the control of the controller C5 of the bio-optical property measurement device 1A. This light L1 is emitted from the light emitting portion 2*p* of the irradiation unit 2 of the first probe 6 to irradiate the subject H. Here, in the biometric apparatus 100, the time resolution measurement method is implemented to measure hemoglobin dynamics of the subject H. Therefore, here, a plurality of (for example, three) light rays L1, which are pulsed light rays and have different wavelengths, are sequentially irradiated. The wavelengths of the light L1 are, for example, 760 nm, 800 nm, and 830 nm.

Similarly, the light L2 is emitted from the light emitting portion 2*p* of the irradiation unit 2 of the second probe 7 to irradiate the subject H. Here, a plurality of (for example, three similarly to the light L1) light rays L2, which are pulsed light rays and have different wavelengths, are sequentially irradiated. The wavelengths of the light L2 are, for example, similar to those of the light L1, and are, as an example, 760 nm, 800 nm, and 830 nm. Irradiation with the light L1 and irradiation with the light L2 are performed at times shifted from each other.

Further, the light L1 propagated inside the subject H is detected by the detection unit 3 of the second probe 7 and output to the light detector C2 of the bio-optical property measurement device 1A. In addition, the light L2 propagated inside the subject H is detected by the detection unit 3 of the first probe 6 and output to the light detector C2. Thereafter, based on this detection result (the amount of attenuation, temporal diffusion, etc. of the light L1 and the light L2), the bio-optical property measurement unit C3 and the arithmetic processor C4 of the bio-optical property measurement device 1A derive oxygenated hemoglobin, deoxygenated hemoglobin, tissue oxygen saturation, etc. in the cranium of the subject H. In this way, here, first, two-channel transmission type measurement is performed.

Figure 10:
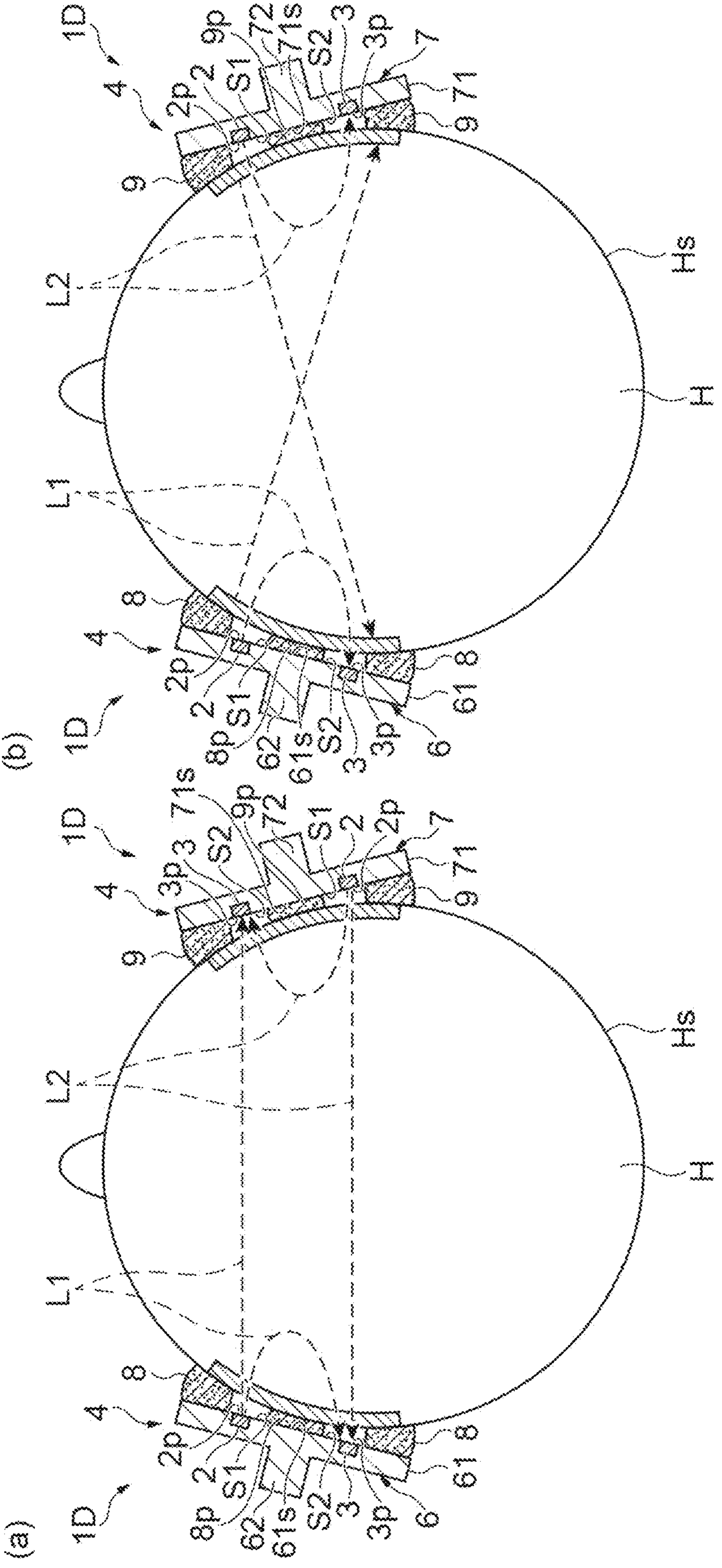
FIGS. 10(*a*) and 10(*b*) are schematic diagrams each illustrating a probe device according to a second embodiment.
Figure 11:
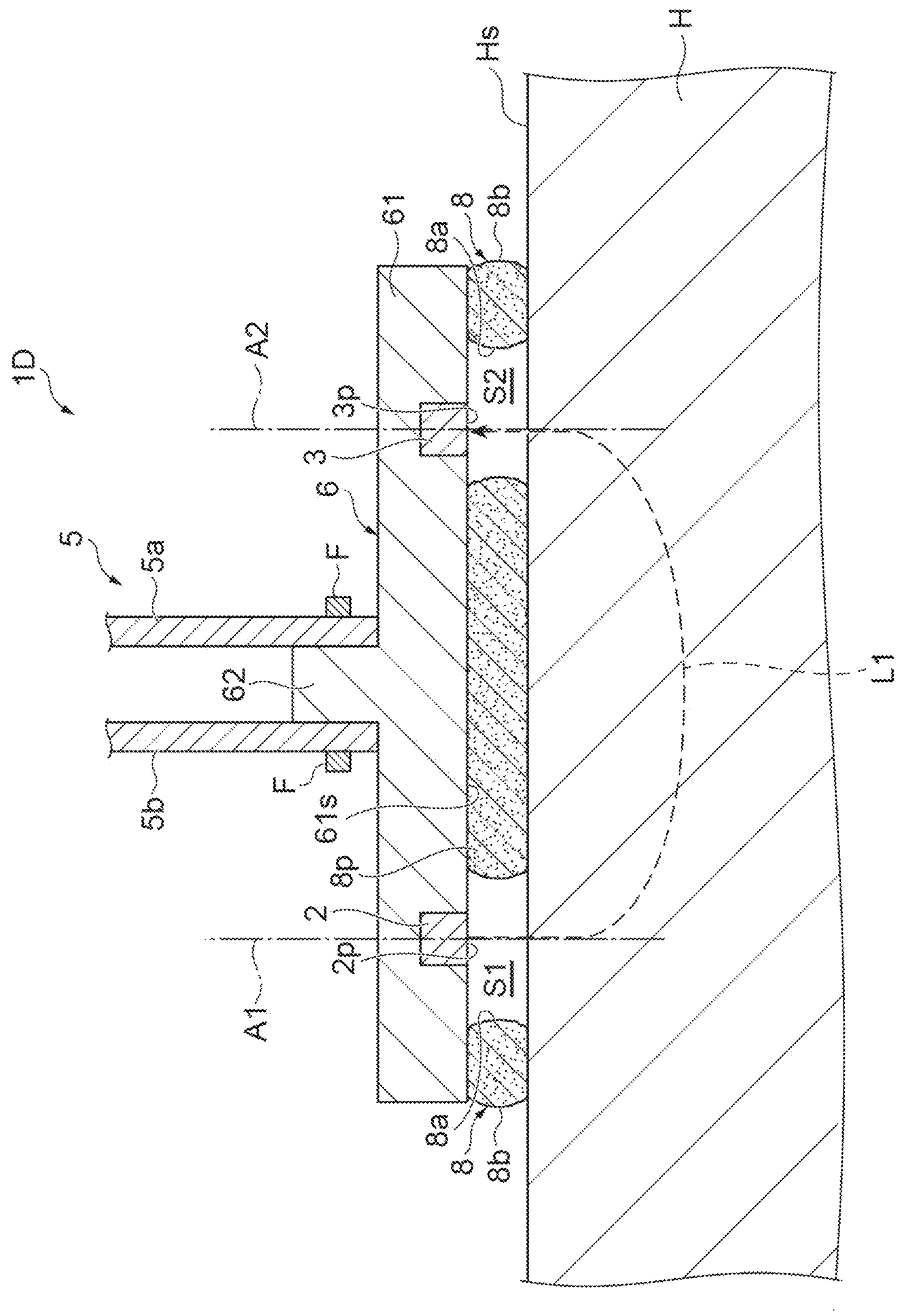
FIG. 11 is a schematic cross-sectional view enlarging and illustrating a part of the probe device to which a probe unit according to the second embodiment is applied.

Note that, in the probe device 1D, positions of the irradiation/detection units in the first probe 6 and the second probe 7 can be set so that two straight lines of a straight line connecting the light emitting portion 2*p* of the irradiation unit 2 of the first probe 6 and the light incidence portion 3*p* of the detection unit 3 of the second probe 7 and a straight line connecting the light incidence portion 3*p* of the detection unit 3 of the first probe 6 and the light emitting portion 2*p* of the irradiation unit 2 of the second probe 7 do not intersect each other (for example, are parallel to each other) (first arrangement, see FIG. 10(*a*)).

Alternatively, in the probe device 1D, the positions of the irradiation/detection units in the first probe 6 and the second probe 7 may be set so that the two straight lines intersect each other (second arrangement, see FIG. 10(*b*)). When the first arrangement is adopted, hemoglobin dynamics can be measured for a wider range inside subject H. When the second arrangement is adopted, hemoglobin dynamics can be measured for a more localized range inside subject H.

Subsequently, reflection type measurement is performed in the biometric apparatus 100 according to the second embodiment. That is, under the control of the controller C5 of the bio-optical property measurement device 1A, the light L1 is provided from the light source C1 to the irradiation unit 2 of the first probe 6, and the light L2 is provided from the light source C1 to the irradiation unit 2 of the second probe 7. This light L1 is emitted from the light emitting portion 2*p* of the irradiation unit 2 of the first probe 6 to irradiate the subject H. Similarly, the light L2 is emitted from the light emitting portion 2*p* of the irradiation unit 2 of the second probe 7 to irradiate the subject H.

The light L1 propagated inside the subject H is detected by the detection unit 3 of the first probe 6 and output to the light detector C2 of the bio-optical property measurement device 1A. In addition, the light L2 propagated inside the subject H is detected by the detection unit 3 of the second probe 7 and output to the light detector C2. Thereafter, based on this detection result (the amount of attenuation, temporal diffusion, etc. of the light L1 and the light L2), the bio-optical property measurement unit C3 and the arithmetic processor C4 of the bio-optical property measurement device 1A derive oxygenated hemoglobin, deoxygenated hemoglobin, tissue oxygen saturation, etc. in the cranium of the subject H. In this way, here, two-channel reflection type measurement is performed.

In this reflection type measurement, light propagated in a superficial part of the subject H is detected, and thus hemoglobin dynamics in the superficial part of the subject H can be measured. Therefore, by considering (excluding) the detection result obtained by reflection type measurement with respect to the detection result obtained by transmission type measurement, it is possible to more accurately measure the hemoglobin dynamics in the deep part of the subject H.

As described above, according to the probe unit 4 according to the second embodiment, it is possible to achieve similar effects to those of the first embodiment. Furthermore, in the probe unit 4 according to the second embodiment, the first surface 61*s* of the first probe 6 further exposes the light incidence portion 3*p* for detecting light propagated inside the subject H, the second surface 71*s* of the second probe 7 further exposes the light emitting portion 2*p* for irradiating the subject H with light, the first light shielding member 8 is attached to the first surface 61*s* to surround the emission axis A1 of the light emitting portion 2*p* and the incidence axis A2 of the light incidence portion 3*p*, and the second light shielding member 9 is attached to the second surface 71*s* to surround the incidence axis A2 of the light incidence portion 3*p* and the emission axis A1 of the light emitting portion 2*p*. For this reason, two-channel measurement is possible using the first probe 6 and the second probe 7.

Further, in the probe unit 4, the first light shielding member 8 includes the portion 8*p* interposed between the light emitting portion 2*p* and the light incidence portion 3*p*, and the second light shielding member 9 includes the portion 9*p* interposed between the light incidence portion 3*p* and the light emitting portion 2*p*. For this reason, the light L1 emitted from the light emitting portion 2*p* of the first probe 6 can be prevented from reflecting off the surface Hs of the subject H and directly entering the light incidence portion 3*p* of the first probe 6. In addition, the light L2 emitted from the light emitting portion 2*p* of the second probe 7 can be prevented from reflecting off the surface Hs of the subject H and directly entering the light incidence portion 3*p* of the second probe 7. Therefore, incidence of light not subjected to detection is suppressed.

The above embodiment describes one aspect of the present disclosure. Therefore, the present disclosure is not limited to the probe unit 4 described above, and may be arbitrarily modified.

Figure 12:
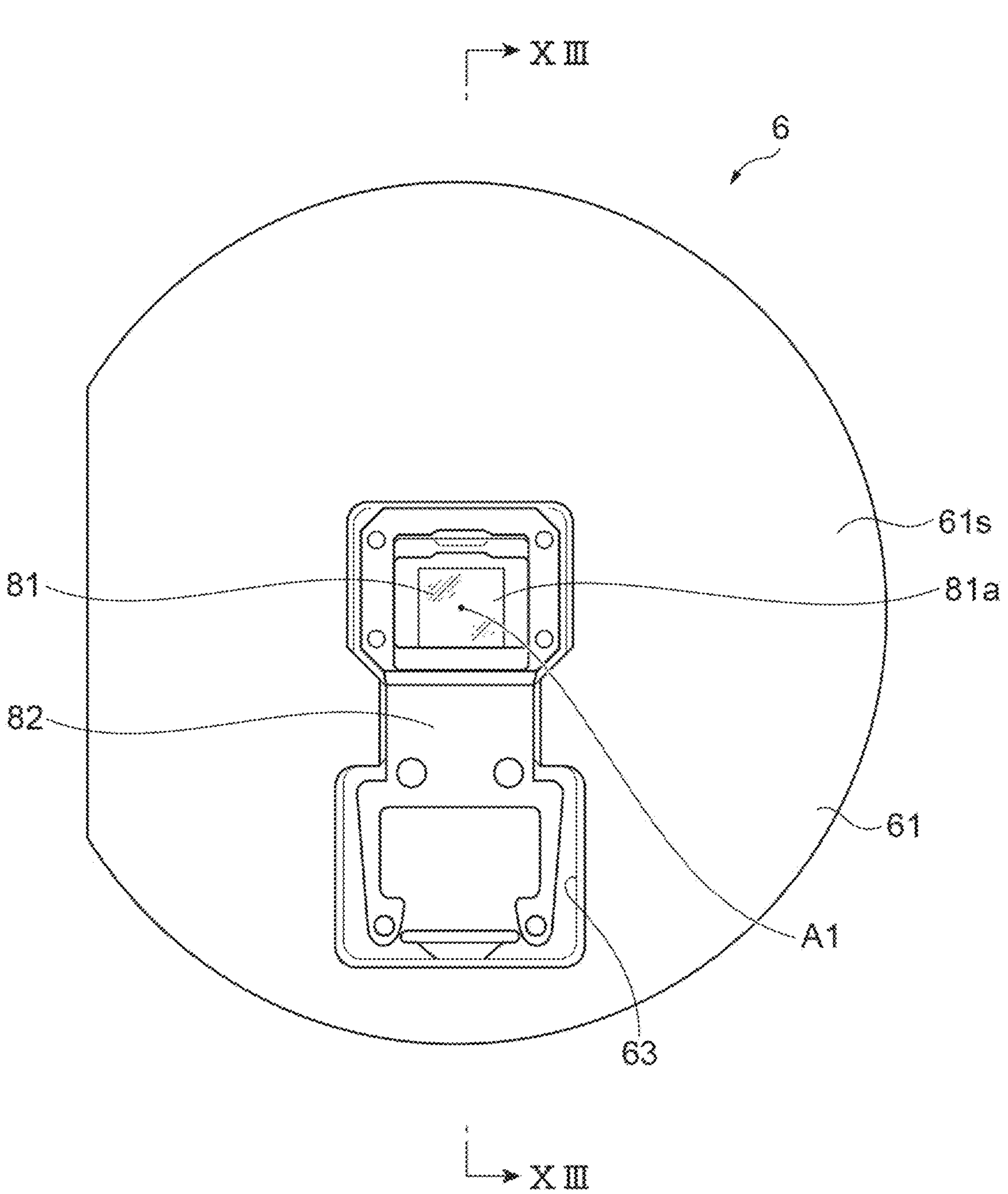
FIG. 12 is a schematic plan view illustrating a first probe according to a modified example.
Figure 13:
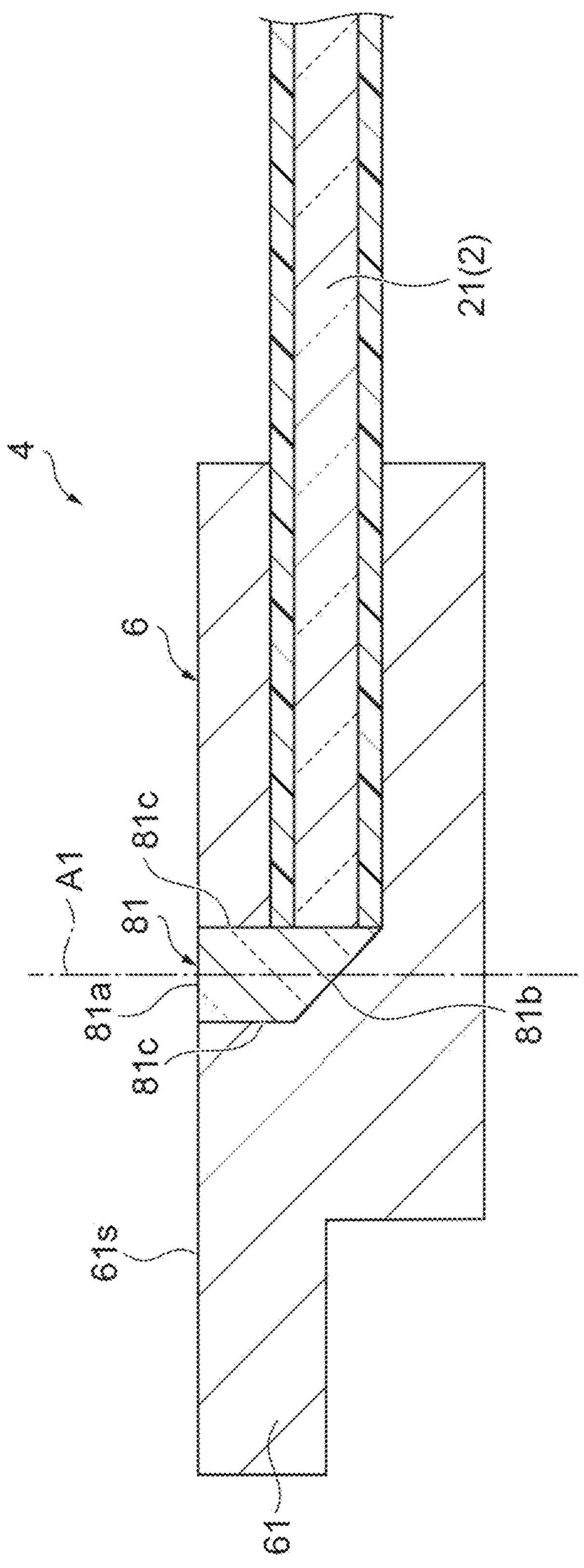
FIG. 13 is a cross-sectional view taken along the line XIII-XIII in FIG. 12.

FIG. 12 is a schematic plan view illustrating a first probe according to a modified example, and FIG. 13 is a cross-sectional view taken along the line XIII-XIII in FIG. 12. In the example illustrated in FIG. 13, some configuration is omitted. For example, in the above embodiment, the light emitting portion 2*p* of the irradiation unit 2 includes the end face 21*s* of the optical fiber 21, and the end face 21*s* is exposed on the first surface 61*s* of the first probe 6. However, as illustrated in FIG. 12, the light emitting portion 2*p* of the irradiation unit 2 may include an end face of another optical member (here an end face 81*a* of a prism 81) coupled to the optical fiber 21, and the end face may be exposed on the first surface 61*s* of the first probe 6.

In this case, the prism 81 is fit into the recess 63 of the holding portion 61 via a case 82. As illustrated in FIG. 13, the optical fiber 21 is coupled to the prism 81 by being connected to (brought into contact with) a side surface of the prism 81 different from the end face 81*a*. More specifically, the prism 81 has a reflective surface 81*b* provided on the opposite side from the end face 81*a* and a side surface 81*c* connecting the end face 81*a* and the reflective surface 81*b* to each other. The optical fiber 21 contacts the side surface 81*c* inside the first probe 6. In this way, light emitted from the optical fiber 21 enters the prism 81 from the side surface 81*c* of the prism 81, is reflected by the reflective surface 81*b*, and is led to the end face 81*a*. The same configuration as that on the first probe 6 side can be adopted as a configuration on the second probe 7 side.

Figure 14:
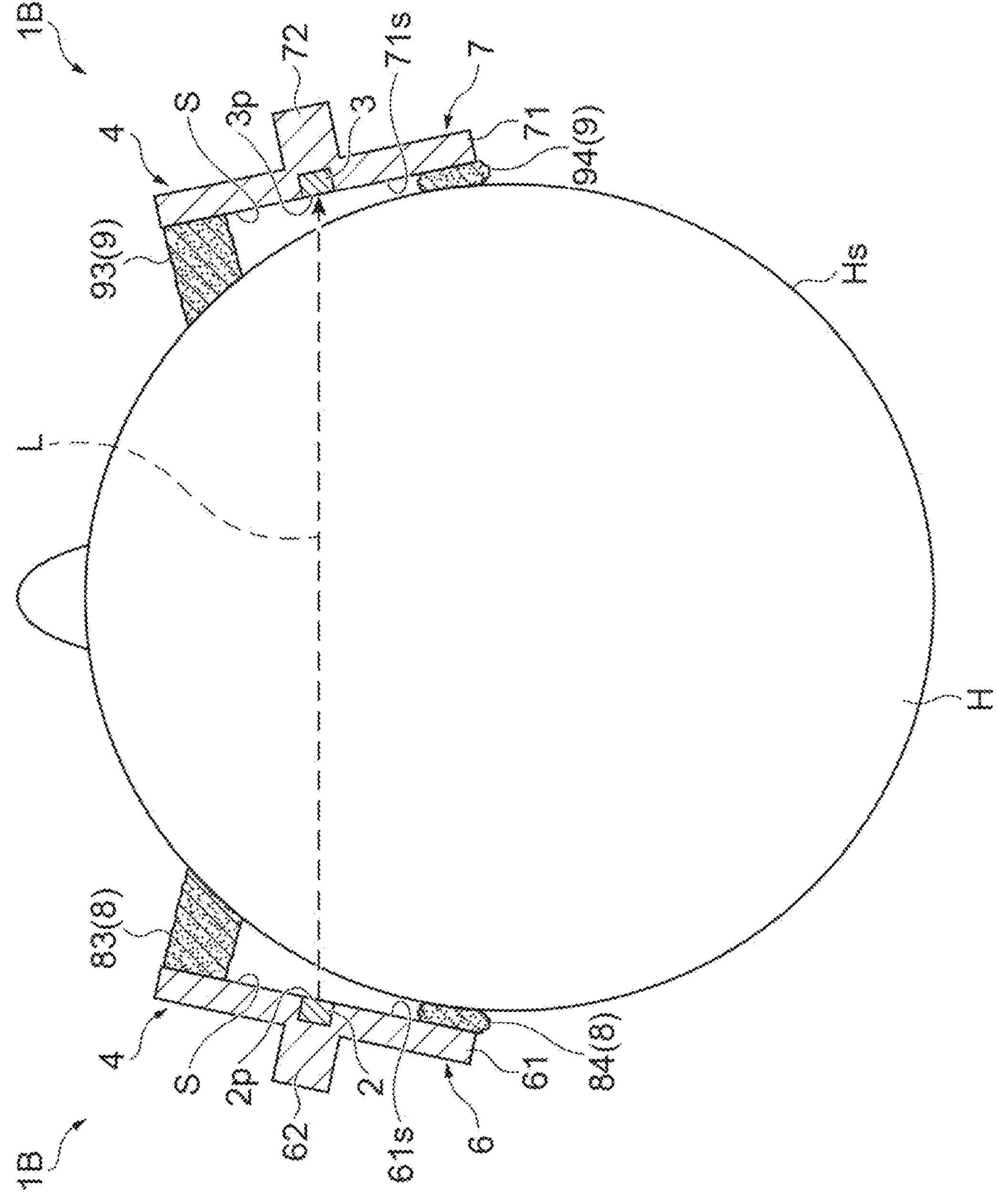
FIG. 14 is a schematic diagram illustrating a probe device according to the modified example.

Further, the above embodiment illustrates the first light shielding member 8 and the second light shielding member 9 having constant thicknesses along the circumferential direction. However, as illustrated in FIG. 14, the thicknesses of the first light shielding member 8 and the second light shielding member 9 may vary along the circumferential direction. More specifically, the first light shielding member 8 may have a relatively thick portion 83 and a relatively thin portion 84, and the second light shielding member 9 may have a relatively thick portion 93 and a relatively thin portion 94. In this case, while the first light shielding member 8 and the second light shielding member 9 are suitably brought into close contact with the subject H according to the outer shape of the subject H, an incident angle of light to the subject H and an incident angle of light from the subject H can be adjusted.

Figure 15:
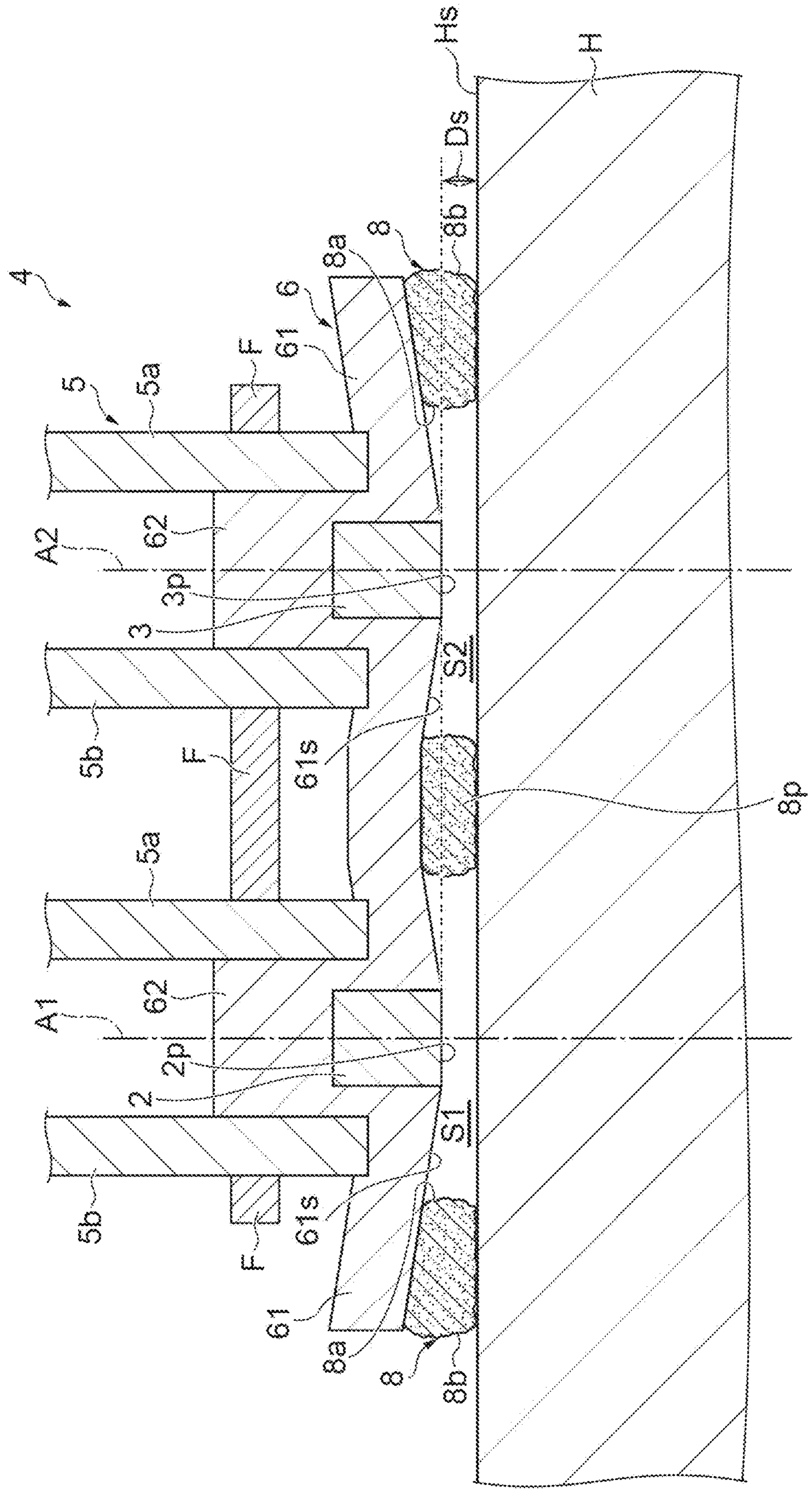
FIG. 15 is a schematic cross-sectional view illustrating a modified example of the probe device according to the second embodiment.

Further, the second embodiment illustrates the main body 5 including the two layer members 5*a* and 5*b* laminated to each other. However, as illustrated in FIG. 15, the main body 5 may include two pairs of layer members 5*a* and 5*b* laminated to each other. In this modified example, a pair of attaching portions 62 and 62 is provided at positions corresponding to the light emitting portion 2*p* and the light incidence portion 3*p*, respectively. One attaching portion 62 is arranged between a pair of layer members 5*a* and 5*b* of the two pairs of layer members 5*a* and 5*b*, and the other attaching portion 62 is arranged between the other pair of layer members 5*a* and 5*b*. Further, in this modified example, the fastener F is inserted through the pair of attaching portions 62 and 62 together with each of the two pairs of layer members 5*a* and 5*b*. In this way, the first probe 6 is attached to the main body 5. The same configuration as that on the first probe 6 side can be adopted as a configuration on the second probe 7 side.

In the probe unit 4 according to this modified example, the main body 5 is attached to the two attaching portions 62. In other words, the first probe 6 is attached to the main body 5 at a plurality of locations. In this way, when the probe unit 4 is attached to the subject H, elastic force applied from the main body 5 to the subject H can be dispersed. As a result, for example, uneven distribution (for example, warping) of the deformation amount of the main body 5 due to the elastic force is suppressed.

Further, the configuration of the irradiation/detection unit is not limited to a configuration in which light is transmitted and received to and from the bio-optical property measurement device 1A using an optical fiber as described above. For example, the irradiation unit 2 may include a light emitting element corresponding to the light source C1, and may be configured to transmit and receive electrical signals to and from the bio-optical property measurement device 1A. In this case, the light emitting portion 2*p* of the irradiation unit 2 can include a light emitting surface of the light emitting element (or an end face of an optical member coupled to the light emitting surface).

Alternatively, the detection unit 3 may include a light receiving element corresponding to the light detector C2, and may be configured to transmit and receive electrical signals to and from the bio-optical property measurement device 1A. In this case, the light incidence portion 3*p* of the detection unit 3 can include a light incidence surface of the light receiving element (or an end face of an optical member coupled to the light incidence surface). In these cases, a communication line for transmitting and receiving electrical signals, a power line for supplying power to the light emitting element or the light receiving element, etc. may be arranged in the groove 64 of the holding portion 61 of the first probe 6, the groove 74 of the holding portion 71 of the second probe 7, etc.

Further, in these cases, the light source C1 and the light detector C2 can be omitted from the bio-optical property measurement device 1A. Furthermore, the irradiation unit 2 and the detection unit 3 may be provided with communication units for wirelessly transmitting and receiving electrical signals to and from the bio-optical property measurement device 1A. In addition, the irradiation unit 2 and the detection unit 3 may be provided with a battery and other elements of the bio-optical property measurement device 1A.

REFERENCE SIGNS LIST

2*p*: light emitting portion (first light emitting portion and second light emitting portion), 3*p*: light incidence portion (first light incidence portion and second light incidence portion), 4: probe unit, 5: main body, 5*a*, 5*b*: layer member, 6: first probe, 7: second probe, 8: first light shielding member, 8*p*: portion (first portion), 9: second light shielding member, 9*p*: portion (second portion), 10: shape memory member, 21, 31: optical fiber, 51: first support, 52: second support, 53: coupling portion, 54, 55: fixing member, 61*s*: first surface (first face), 71*s*: second surface (second face), A1: emission axis, A2: incidence axis, G: gap (fiber holding portion), H: subject, L, L1, L2: light.

The invention claimed is:

1. A probe unit used to measure hemoglobin dynamics inside a subject, the probe unit comprising:

a main body having flexibility;

a first probe attached to the main body and having a first face from which a first light emitting portion configured to irradiate the subject with light is exposed, the first light emitting portion having a first emission axis;

a second probe attached to the main body to face the first probe and having a second face from which a first light incidence portion configured to detect light propagated inside the subject is exposed, the first light incidence portion having a first incidence axis;

a first light shielding member having light shielding properties, containing an elastic material, and attached to the first face to surround the first emission axis of the first light emitting portion; and a second light shielding member having light shielding properties, containing an elastic material, and attached to the second face to surround the first incidence axis of the first light incidence portion, wherein:

the first face of the first probe further exposes a second light incidence portion configured to detect light propagated inside the subject, the second light incidence portion having a second incidence axis;

the second face of the second probe further exposes a second light emitting portion configured to irradiate the subject with light, the second light emitting portion having a second emission axis;

the first light shielding member is attached to the first face to surround the first emission axis of the first light emitting portion and the second incidence axis of the second light incidence portion; and the second light shielding member is attached to the second face to surround the first incidence axis of the first light incidence portion and the second emission axis of the second light emitting portion.

2. The probe unit according to claim 1, wherein each of the first probe and the second probe is rotatably provided with respect to the main body.

3. The probe unit according to claim 1, wherein:

the first light shielding member includes a first portion interposed between the first light emitting portion and the second light incidence portion of the first probe; and the second light shielding member includes a second portion interposed between the first light incidence portion and the second light emitting portion of the second probe.

4. The probe unit according to claim 1, further comprising a shape memory member, wherein:

the main body includes a first support configured to support the first probe, a second support configured to support the second probe, and a coupling portion configured to couple the first support and the second support; and the shape memory member is provided in the coupling portion.

5. The probe unit according to claim 1, wherein the main body includes:

a plurality of layer members laminated to each other; and a fixing member configured to detachably fix the plurality of layer members to each other.

6. The probe unit according to claim 1, wherein:

the first probe and the second probe each include an optical fiber; and the main body includes a fiber holding portion through which the optical fiber is inserted and configured to hold the optical fiber.

7. The probe unit according to claim 1, wherein the main body is made of rubber sponge.

* * * * *